United States Patent
Mulligan-Kehoe et al.

(10) Patent No.: US 7,510,714 B2
(45) Date of Patent: Mar. 31, 2009

(54) METHODS FOR MODULATING ANGIOGENESIS

(75) Inventors: Mary Jo Mulligan-Kehoe, Enfield, NH (US); Richard J. Powell, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 11/668,663

(22) Filed: Jan. 30, 2007

(65) Prior Publication Data
US 2007/0191277 A1 Aug. 16, 2007

Related U.S. Application Data

(63) Continuation-in-part of application No. 10/506,225, filed as application No. PCT/US03/09981 on Apr. 1, 2003, now Pat. No. 7,241,446.

(60) Provisional application No. 60/369,392, filed on Apr. 1, 2002, provisional application No. 60/448,301, filed on Feb. 14, 2003.

(51) Int. Cl.
*A61K 38/16* (2006.01)
*A61K 38/17* (2006.01)

(52) U.S. Cl. ................. 424/184.1; 424/185.1

(58) Field of Classification Search ........................ None
See application file for complete search history.

(56) References Cited

U.S. PATENT DOCUMENTS 6,235,713 B1   5/2001   Achen et al.
7,241,446 B2 *  7/2007   Mulligan-Kehoe et al. ............. 424/184.1
7,306,803 B2 * 12/2007   Mulligan-Kehoe ....... 424/185.1

OTHER PUBLICATIONS

Mulligan-Kehoe et al, J Biol Chem 276(11): 8588-8596, Mar. 2001.*
Daugherty et al, Am J Med Sci 323(1): 3-10, Jan. 2002.*
Derma et al, Biotechnology 12: 320, 1994.*
Ngo et al, in The Protein Folding Problem and Tertiary Structure Prediction, pp. 492-495, 1994.*
Mason et al, Molecular Endocrinology 8(3): 325-332, 1994.*
Standing et al, Curr Opin Struct Biol 13(5):595-601, Oct. 2003.*
Kang et al., "Cloning and characterization of human ubiquitin-processing protease-43 from terminally differentiated human melanoma cells using a rapid subtraction hybridization protocol RaSH", Gene 2001 267:233-242.
Kitareewan et al., "UBE1L is a retinoid target that triggers PML/RARalpha degradation and apoptosis in acute promyelocytic leukemia", Proc Natl Acad Sci USA 2002 99(6):3806-3811.
Mulligan-Kehoe et al., "A Truncated Plasminogen Activator Inhibitor-1 Protein Blocks the Availability of Heparin-binding Vascular Endothelial Growth Factor A Isoforms", J Biol Chem 2002 277(5):49077-49089.

* cited by examiner

*Primary Examiner*—Phuong Huynh
(74) *Attorney, Agent, or Firm*—Licata & Tyrrell P.C.

(57) ABSTRACT

Recombinant plasminogen activator inhibitor-1 (PAI-1) isoforms which lack the reactive center loop and contain the complete heparin-binding domain or lack at least a portion of the heparin-binding domain are described. The rPAI-1 isoforms disclosed herein may be used to modulate angiogenesis through blocking release of VEGF from a VEGF-heparin complex. Furthermore, the rPAI-1 proteins may be used to inhibit cell proliferation and migration, induce apoptosis, and produce proteolytic fragments corresponding to angiostatin kringles 1-3 and kringles 1-4. A truncated proteolytic plasmin protein of 34 kDa is also provided.

5 Claims, 2 Drawing Sheets

HUMAN PAI-1

Vn  Hep  uPA, tPA  uPA, tPA

| HEPARIN | UROKINASE 110-145 | uPA 128-145 | uPA 346 |
| 80-88 | FIBRIN 110 & 145 | tPA 128-145 | tPA 346 |
| Lys-Lys | THROMBIN 115-148 | | |
| | VITRONECTIN (Vn) 110-145 | | |

PORCINE PAI-1

5'-UTR                                    RCL  3'-UTR

Vn  Hep  uPA, tPA  uPA, tPA rPAI-1$_{24}$ rPAI-1$_{23}$ rPAI-1$_{\Delta 23}$ rPAI-1$_{Hep23}$

SEQUENCE LISTING

<160> NUMBER OF SEQ ID NOS: 20

<210> SEQ ID NO 1
<211> LENGTH: 202
<212> TYPE: PRT
<213> ORGANISM: Homo sapiens

<400> SEQUENCE: 1

```
Met Gly Phe Lys Ile Asp Asp Lys Gly Met Ala Pro Ala Leu Arg His
1               5                   10                  15

Leu Tyr Lys Glu Leu Met Gly Pro Trp Asn Lys Asp Glu Ile Ser Thr
            20                  25                  30

Thr Asp Ala Ile Phe Val Gln Arg Asp Leu Lys Leu Val Gln Gly Phe
        35                  40                  45

Met Pro His Phe Phe Arg Leu Phe Arg Ser Thr Val Lys Gln Val Asp
    50                  55                  60

Phe Ser Glu Val Glu Arg Ala Arg Phe Ile Ile Asn Asp Trp Val Lys
65                  70                  75                  80

Thr His Thr Lys Gly Met Ile Ser Asn Leu Leu Gly Lys Gly Ala Val
                85                  90                  95

Asp Gln Leu Thr Arg Leu Val Leu Val Asn Ala Leu Tyr Phe Asn Gly
            100                 105                 110

Gln Trp Lys Thr Pro Phe Pro Asp Ser Ser Thr His Arg Arg Leu Phe
        115                 120                 125

His Lys Ser Asp Gly Ser Thr Val Ser Val Pro Met Met Ala Gln Thr
```

```
                130                 135                 140
Asn Lys Phe Asn Tyr Thr Glu Phe Thr Thr Pro Asp Gly His Tyr Tyr
145                 150                 155                 160

Asp Ile Leu Glu Leu Pro Tyr His Gly Asp Thr Leu Ser Met Phe Ile
                165                 170                 175

Ala Ala Pro Tyr Glu Lys Glu Val Pro Leu Ser Ala Leu Thr Asn Ile
                180                 185                 190

Leu Ser Ala Gln Leu Ile Ser His Trp Lys
                195                 200

<210> SEQ ID NO 2
<211> LENGTH: 297
<212> TYPE: PRT
<213> ORGANISM: Homo sapiens

<400> SEQUENCE: 2

Met Gly Pro Trp Asn Lys Asp Glu Ile Ser Thr Thr Asp Ala Ile Phe
1               5                   10                  15

Val Gln Arg Asp Leu Lys Leu Val Gln Gly Phe Met Pro His Phe Phe
                20                  25                  30

Arg Leu Phe Arg Ser Thr Val Lys Gln Val Asp Phe Ser Glu Val Glu
                35                  40                  45

Arg Ala Arg Phe Ile Ile Asn Asp Trp Val Lys Thr His Thr Lys Gly
            50                  55                  60

Met Ile Ser Asn Leu Leu Gly Lys Gly Ala Val Asp Gln Leu Thr Arg
65                  70                  75                  80

Leu Val Leu Val Asn Ala Leu Tyr Phe Asn Gly Gln Trp Lys Thr Pro
                85                  90                  95

Phe Pro Asp Ser Ser Thr His Arg Arg Leu Phe His Lys Ser Asp Gly
                100                 105                 110

Ser Thr Val Ser Val Pro Met Met Ala Gln Thr Asn Lys Phe Asn Tyr
                115                 120                 125

Thr Glu Phe Thr Thr Pro Asp Gly His Tyr Tyr Asp Ile Leu Glu Leu
                130                 135                 140

Pro Tyr His Gly Asp Thr Leu Ser Met Phe Ile Ala Ala Pro Tyr Glu
145                 150                 155                 160

Lys Glu Val Pro Leu Ser Ala Leu Thr Asn Ile Leu Ser Ala Gln Leu
                165                 170                 175

Ile Ser His Trp Lys Gly Asn Met Thr Arg Leu Pro Arg Leu Leu Val
                180                 185                 190

Leu Pro Lys Phe Ser Leu Glu Thr Glu Val Asp Leu Arg Lys Pro Leu
                195                 200                 205

Glu Asn Leu Gly Met Thr Asp Met Phe Arg Gln Phe Gln Ala Asp Phe
210                 215                 220

Thr Ser Leu Ser Asp Gln Glu Pro Leu His Val Ala Gln Ala Leu Gln
225                 230                 235                 240

Lys Val Lys Ile Glu Val Asn Glu Ser Gly Thr Val Ala Ser Ser Ser
                245                 250                 255

Thr Ala Val Ile Val Ser Ala Arg Met Ala Pro Glu Glu Ile Ile Met
                260                 265                 270

Asp Arg Pro Phe Leu Phe Val Val Arg His Asn Pro Thr Gly Thr Val
                275                 280                 285

Leu Phe Met Gly Gln Val Met Glu Pro
                290                 295
```

<210> SEQ ID NO 3
<211> LENGTH: 175
<212> TYPE: PRT
<213> ORGANISM: Homo sapiens

<400> SEQUENCE: 3

Asp Glu Ile Ser Thr Thr Asp Ala Ile Phe Val Gln Arg Asp Leu Lys
1               5                   10                  15

Leu Val Gln Gly Phe Met Pro His Phe Arg Leu Phe Arg Ser Thr
            20                  25                  30

Val Lys Gln Val Asp Phe Ser Glu Val Glu Arg Ala Arg Phe Ile Ile
        35                  40                  45

Asn Asp Trp Val Lys Thr His Thr Lys Gly Met Ile Ser Asn Leu Leu
    50                  55                  60

Gly Lys Gly Ala Val Asp Gln Leu Thr Arg Leu Val Leu Val Asn Ala
65                  70                  75                  80

Leu Tyr Phe Asn Gly Gln Trp Lys Thr Pro Phe Pro Asp Ser Ser Thr
                85                  90                  95

His Arg Arg Leu Phe His Lys Ser Asp Gly Ser Thr Val Ser Val Pro
            100                 105                 110

Met Met Ala Gln Thr Asn Lys Phe Asn Tyr Thr Glu Phe Thr Thr Pro
        115                 120                 125

Asp Gly His Tyr Tyr Asp Ile Leu Glu Leu Pro Tyr His Gly Asp Thr
    130                 135                 140

Leu Ser Met Phe Ile Ala Ala Pro Tyr Glu Lys Glu Val Pro Leu Ser
145                 150                 155                 160

Ala Leu Thr Asn Ile Leu Ser Ala Gln Leu Ile Ser His Trp Lys
                165                 170                 175

<210> SEQ ID NO 4
<211> LENGTH: 181
<212> TYPE: PRT
<213> ORGANISM: Homo sapiens

<400> SEQUENCE: 4

Met Gly Pro Trp Asn Lys Asp Glu Ile Ser Thr Thr Asp Ala Ile Phe
1               5                   10                  15

Val Gln Arg Asp Leu Lys Leu Val Gln Gly Phe Met Pro His Phe Phe
            20                  25                  30

Arg Leu Phe Arg Ser Thr Val Lys Gln Val Asp Phe Ser Glu Val Glu
        35                  40                  45

Arg Ala Arg Phe Ile Ile Asn Asp Trp Val Lys Thr His Thr Lys Gly
    50                  55                  60

Met Ile Ser Asn Leu Leu Gly Lys Gly Ala Val Asp Gln Leu Thr Arg
65                  70                  75                  80

Leu Val Leu Val Asn Ala Leu Tyr Phe Asn Gly Gln Trp Lys Thr Pro
                85                  90                  95

Phe Pro Asp Ser Ser Thr His Arg Arg Leu Phe His Lys Ser Asp Gly
            100                 105                 110

Ser Thr Val Ser Val Pro Met Met Ala Gln Thr Asn Lys Phe Asn Tyr
        115                 120                 125

Thr Glu Phe Thr Thr Pro Asp Gly His Tyr Tyr Asp Ile Leu Glu Leu
    130                 135                 140

Pro Tyr His Gly Asp Thr Leu Ser Met Phe Ile Ala Ala Pro Tyr Glu
145                 150                 155                 160

```
Lys Glu Val Pro Leu Ser Ala Leu Thr Asn Ile Leu Ser Ala Gln Leu
            165                 170                 175

Ile Ser His Trp Lys
            180

<210> SEQ ID NO 5
<211> LENGTH: 202
<212> TYPE: PRT
<213> ORGANISM: Sus scrofa

<400> SEQUENCE: 5

Met Gln Phe Lys Ile Glu Glu Lys Gly Met Ala Pro Ala Leu Arg Gln
1               5                   10                  15

Leu Tyr Lys Glu Leu Met Gly Pro Trp Asn Lys Asp Glu Ile Ser Thr
            20                  25                  30

Ala Asp Ala Ile Phe Val Gln Arg Asp Leu Lys Leu Val Gln Gly Phe
        35                  40                  45

Met Pro Tyr Phe Phe Arg Leu Phe Arg Thr Thr Val Lys Gln Val Asp
    50                  55                  60

Phe Ser Glu Met Asp Arg Ala Arg Phe Ile Ile Asn Asp Trp Val Lys
65                  70                  75                  80

Arg His Thr Lys Gly Met Ile Asn Asp Leu Leu Gly Gln Gly Ala Val
                85                  90                  95

Asp Gln Leu Thr Arg Leu Val Leu Val Asn Ala Leu Tyr Phe Asn Gly
            100                 105                 110

Gln Trp Lys Thr Pro Phe Pro Glu Lys Ser Thr His His Arg Leu Phe
        115                 120                 125

His Lys Ser Asp Gly Ser Thr Val Ser Val Pro Met Met Ala Gln Thr
    130                 135                 140

Asn Lys Phe Asn Tyr Thr Glu Phe Ser Thr Pro Asp Gly His Tyr Tyr
145                 150                 155                 160

Asp Ile Leu Glu Leu Pro Tyr His Gly Asn Thr Leu Ser Met Phe Ile
                165                 170                 175

Ala Ala Pro Tyr Glu Lys Glu Val Pro Leu Ser Ala Leu Thr Ser Ile
            180                 185                 190

Leu Asp Ala Gln Leu Ile Ser Gln Trp Lys
        195                 200

<210> SEQ ID NO 6
<211> LENGTH: 297
<212> TYPE: PRT
<213> ORGANISM: Sus scrofa

<400> SEQUENCE: 6

Met Gly Pro Trp Asn Lys Asp Glu Ile Ser Thr Ala Asp Ala Ile Phe
1               5                   10                  15

Val Gln Arg Asp Leu Lys Leu Val Gln Gly Phe Met Pro Tyr Phe Phe
            20                  25                  30

Arg Leu Phe Arg Thr Thr Val Lys Gln Val Asp Phe Ser Glu Met Asp
        35                  40                  45

Arg Ala Arg Phe Ile Ile Asn Asp Trp Val Lys Arg His Thr Lys Gly
    50                  55                  60

Met Ile Asn Asp Leu Leu Gly Gln Gly Ala Val Asp Gln Leu Thr Arg
65                  70                  75                  80

Leu Val Leu Val Asn Ala Leu Tyr Phe Asn Gly Gln Trp Lys Thr Pro
                85                  90                  95
```

```
Phe Pro Glu Lys Ser Thr His His Arg Leu Phe His Lys Ser Asp Gly
        100                 105                 110

Ser Thr Val Ser Val Pro Met Met Ala Gln Thr Asn Lys Phe Asn Tyr
            115                 120                 125

Thr Glu Phe Ser Thr Pro Asp Gly His Tyr Tyr Asp Ile Leu Glu Leu
        130                 135                 140

Pro Tyr His Gly Asn Thr Leu Ser Met Phe Ile Ala Ala Pro Tyr Glu
145                 150                 155                 160

Lys Glu Val Pro Leu Ser Ala Leu Thr Ser Ile Leu Asp Ala Gln Leu
                165                 170                 175

Ile Ser Gln Trp Lys Gly Asn Met Thr Arg Leu Thr Arg Leu Leu Val
            180                 185                 190

Leu Pro Lys Phe Ser Leu Glu Ser Glu Val Asp Leu Arg Arg Pro Leu
        195                 200                 205

Glu Asn Leu Gly Met Thr Asp Met Phe Arg Pro Asn Gln Ala Asp Phe
    210                 215                 220

Ser Ser Leu Ser Asp Gln Glu Leu Leu Tyr Met Ser Gln Ala Leu Gln
225                 230                 235                 240

Lys Val Lys Ile Glu Val Asn Glu Ser Gly Thr Val Ala Ser Ser Ser
                245                 250                 255

Thr Ala Ile Ile Val Ser Ala Arg Met Ala Pro Glu Glu Ile Ile Met
            260                 265                 270

Asp Arg Pro Phe Leu Phe Val Val Arg His Asn Pro Thr Gly Thr Val
        275                 280                 285

Leu Phe Met Gly Gln Val Met Glu Pro
    290                 295

<210> SEQ ID NO 7
<211> LENGTH: 175
<212> TYPE: PRT
<213> ORGANISM: Sus scrofa

<400> SEQUENCE: 7

Asp Glu Ile Ser Thr Ala Asp Ala Ile Phe Val Gln Arg Asp Leu Lys
1               5                   10                  15

Leu Val Gln Gly Phe Met Pro Tyr Phe Phe Arg Leu Phe Arg Thr Thr
            20                  25                  30

Val Lys Gln Val Asp Phe Ser Glu Met Asp Arg Ala Arg Phe Ile Ile
        35                  40                  45

Asn Asp Trp Val Lys Arg His Thr Lys Gly Met Ile Asn Asp Leu Leu
    50                  55                  60

Gly Gln Gly Ala Val Asp Gln Leu Thr Arg Leu Val Leu Val Asn Ala
65                  70                  75                  80

Leu Tyr Phe Asn Gly Gln Trp Lys Thr Pro Phe Pro Glu Lys Ser Thr
                85                  90                  95

His His Arg Leu Phe His Lys Ser Asp Gly Ser Thr Val Ser Val Pro
            100                 105                 110

Met Met Ala Gln Thr Asn Lys Phe Asn Tyr Thr Glu Phe Ser Thr Pro
        115                 120                 125

Asp Gly His Tyr Tyr Asp Ile Leu Glu Leu Pro Tyr His Gly Asn Thr
    130                 135                 140

Leu Ser Met Phe Ile Ala Ala Pro Tyr Glu Lys Glu Val Pro Leu Ser
145                 150                 155                 160

Ala Leu Thr Ser Ile Leu Asp Ala Gln Leu Ile Ser Gln Trp Lys
                165                 170                 175
```

```
<210> SEQ ID NO 8
<211> LENGTH: 181
<212> TYPE: PRT
<213> ORGANISM: Sus scrofa

<400> SEQUENCE: 8

Met Gly Pro Trp Asn Lys Asp Glu Ile Ser Thr Ala Asp Ala Ile Phe
1               5                   10                  15

Val Gln Arg Asp Leu Lys Leu Val Gln Gly Phe Met Pro Tyr Phe Phe
            20                  25                  30

Arg Leu Phe Arg Thr Thr Val Lys Gln Val Asp Phe Ser Glu Met Asp
        35                  40                  45

Arg Ala Arg Phe Ile Ile Asn Asp Trp Val Lys Arg His Thr Lys Gly
    50                  55                  60

Met Ile Asn Asp Leu Leu Gly Gln Gly Ala Val Asp Gln Leu Thr Arg
65                  70                  75                  80

Leu Val Leu Val Asn Ala Leu Tyr Phe Asn Gly Gln Trp Lys Thr Pro
                85                  90                  95

Phe Pro Glu Lys Ser Thr His His Arg Leu Phe His Lys Ser Asp Gly
            100                 105                 110

Ser Thr Val Ser Val Pro Met Met Ala Gln Thr Asn Lys Phe Asn Tyr
        115                 120                 125

Thr Glu Phe Ser Thr Pro Asp Gly His Tyr Tyr Asp Ile Leu Glu Leu
    130                 135                 140

Pro Tyr His Gly Asn Thr Leu Ser Met Phe Ile Ala Ala Pro Tyr Glu
145                 150                 155                 160

Lys Glu Val Pro Leu Ser Ala Leu Thr Ser Ile Leu Asp Ala Gln Leu
                165                 170                 175

Ile Ser Gln Trp Lys
            180

<210> SEQ ID NO 9
<211> LENGTH: 27
<212> TYPE: PRT
<213> ORGANISM: Sus scrofa

<400> SEQUENCE: 9

Met Gln Phe Lys Ile Glu Glu Lys Gly Met Ala Pro Ala Leu Arg Gln
1               5                   10                  15

Leu Tyr Lys Glu Leu Met Gly Pro Trp Asn Lys
            20                  25

<210> SEQ ID NO 10
<211> LENGTH: 24
<212> TYPE: PRT
<213> ORGANISM: Sus scrofa

<400> SEQUENCE: 10

Lys Ile Glu Glu Lys Gly Met Ala Pro Ala Leu Arg Gln Leu Tyr Lys
1               5                   10                  15

Glu Leu Met Gly Pro Trp Asn Lys
            20

<210> SEQ ID NO 11
<211> LENGTH: 3000
<212> TYPE: DNA
<213> ORGANISM: Sus scrofa
```

```
<400> SEQUENCE: 11
gaattcggca cgagtgcaga gtcaagaacg ctgtcaaggg agccacaccc cctggcccgc      60
agaggaatcg ccgtcagcaa gaggcagcaa gaggattgag tcgccagcca gttacaaggc     120
accttgagac tttcaggatg cggatgtcgc tggtctttgc ctgcctagcg atgggcctgg     180
cccttacctt tgccgaaggc tctgcctcct cccatcacca gtctctggca gcccgcctgg     240
ccacagactt tggagtgaag gtgtttcggc aggtggtaca ggcctccaag gaccgcaacg     300
tggttttctc accctatggg gtggcctccg tcctggccat gctgcagctg accacggcgg     360
gagacaccca gcagcagatc caagaggcca tgcagttcaa gattgaggag aagggcatgg     420
ccctgccct ccgtcaactg tacaaggagc tcatggggcc gtggaacaaa gatgagatca     480
gcacggccga tgccatcttc gtgcagcggg atctgaagct ggtccagggt ttcatgccct     540
acttcttcag gctgttccgg accacggtca agcaggtgga ttttcagag atggacagag     600
ccaggttcat catcaatgac tgggtgaaga gacacacaaa aggcatgatc aatgacttac     660
ttggccaagg ggctgtggac cagctgacgc gcctggttct ggtgaatgcc ctctacttca     720
acggccagtg gaaaacgccc ttcccagaga aaagcactca ccaccgcctc ttccacaagt     780
ctgatggcag caccgtctct gtgcccatga tggctcagac caacaagttc aactacactg     840
agttttccac ccccgacggc cattactacg acatcctgga attgcctac acggcaaca     900
ctctgagcat gttcattgcc gcccctacg aaaagaggt gcctctctcc gccctcacca     960
gcattctgga cgctcagctc atcagccagt ggaaagggaa tatgaccaga ctcacccgcc    1020
tcctggttct gcccaagttc tccctggaga gtgaagttga cctcaggagg cccctggaga    1080
acttgggaat gacggatatg tttaggccta accaggcgga cttctcaagt ctttcagatc    1140
aagagcttct gtacatgtcg caggccctgc aaaaggtgaa gatcgaggtg aatgagagcg    1200
gcacggtggc atcctcctct acggccatta tcgtctcagc ccgcatggcc ccgaggaga    1260
tcatcatgga ccggcccttc ctgttcgtgg tgcggcacaa cccacagga acggtccttt    1320
tcatgggcca agtgatggag ccttgaccat ggatggaaaa gcagtcctcg aatgggacag    1380
aactggagat atccaggaag aagaatctcc ggagagaatt ttcactttaa gtcattttgc    1440
tggagaaaaa gaagctattt gcccttgttt tcataatggt aaaaattctt tcgaatctgc    1500
ctcttagacc tcaggctccc caggaagggg agagaggaca ctggagaaaa ctcccccagt    1560
ggaggtcccg ggagagacct tgaagcacgt ctccccaaag ggctggcagc cagaccacag    1620
aactctcaga accactcgcg cagctgcttc tgcccaacgc tctgccattg gggtcttcgg    1680
actggatccc actgtggccc tggcaggata ggagcgcagg cttacaggaa cccctgtgtg    1740
ctgggtagaa atgatttgcg ttccagtcac gttgctgtca ctcttgcgct gtctgccact    1800
gctgagaggg ctggcggtgg cggcccaagg ccaaggcaag aaacaccctt tggtggcaag    1860
gtccgtcctc ccccggccaa gcctccgagg tgcgcgaccc acctgggcct ggctgctccc    1920
tccccagaaa cagtgtgtat gtattatttt ggagtgtagg tgacttgttt acttggagga    1980
gcaggcttct gcttcccaca aacttcattt tgcagaaata gaggaagaaa cgtgaggtgt    2040
ctgcctggat ctcagctcca gtctcccggt ggggagggtg ggatgccagg ggtgtgcttg    2100
aatatttatc atatccttgc ccttgtgtgc ttgttagaga gaaagagggt tatagagaag    2160
acatattatt taaacttgtt catagtgttc ctttgtggtc tgtgtggttg catctcagga    2220
ctcccggcca cttgtcgcct gtggggtggc aagcgtgatg gggcccccaca ctgccacctg    2280
gtggctgcct gaacccccatt gctcctctct tttccttgtt tttccacttg atggaggagg    2340
```

-continued

```
acccctgcca ggattattca acttcagccc acttgaggga ccaaagggat ggaggggcag   2400
ggttgaaggg agacagagtt gtttccaatc tttccaatat atttaggagc aggcgtgcaa   2460
ggggctacat gacctagcag gacagaactt tccccaatca tagggtgact cacagccgcc   2520
ctggtgactc atttcaatgt gtcatttccg gctgctgtgt gtgagcagtg gacacgtgag   2580
agagggagag aaaatgacag agaatgagag agacagcaag ttcgggctcc actacccca    2640 ttagataatc tttctgcaaa ccagctcgca ggaggttacg gcatgcagac caatttattg   2700
aagaattgca cagagaggtt gaatgaatgt aactaataga actcccacca tcccaccatg   2760
cccttcagtg aaaaatgttc gttcctggca ttttttttc tttttcatt atgcactgga     2820 caatgacagc cacacacgta ccccgagga tacccaaatg tggggtccag cgttcttaaa    2880
attgtgtttt ctatgctttt tcactttga tatagaagca agttaaaaaa aaagttttta    2940 aaaaataat aaataaacac aaaaaagaa tattcaaaaa aaaaaaaaa aaaactcgag       3000
```

<210> SEQ ID NO 12
<211> LENGTH: 1140
<212> TYPE: DNA
<213> ORGANISM: Homo sapiens

<400> SEQUENCE: 12

```
gtgcaccatc ccccatccta cgtggcccac ctggcctcag acttcggggt gagggtgttt   60
cagcaggtgg cgcaggcctc caaggaccgc aacgtggttt tctcacccta tggggtggcc   120
tcggtgttgg ccatgctcca gctgacaaca ggaggagaaa cccagcagca gattcaagca   180
gctatgggat tcaagattga tgacaagggc atggccccg ccctccggca tctgtacaag    240
gagctcatgg ggccatggaa caaggatgag atcagcacca cagacgcgat cttcgtccag   300
cgggatctga agctggtcca gggcttcatg ccccacttct tcaggctgtt ccggagcacg   360
gtcaagcaag tggacttttc agaggtggag agagccagat tcatcatcaa tgactgggtg   420
aagacacaca caaaaggtat gatcagcaac ttgcttggga aggagccgt ggaccagctg    480 acacggctgt tgctggtgaa tgccctctac ttcaacggcc agtggaagac tcccttcccc   540
gactccagca cccaccgccg cctcttccac aaatcagacg gcagcactgt ctctgtgccc   600
atgatggctc agaccaacaa gttcaactat actgagttca ccacgcccga tggccattac   660
tacgacatcc tggaactgcc ctaccacggg gacacctca gcatgttcat tgctgcccct   720
tatgaaaaag aggtgcctct ctctgccctc accaacattc tgagtgccca gctcatcagc   780
cactggaaag gcaacatgac caggctgccc cgcctcctgg ttctgcccaa gttctccctg   840
gagactgaag tcgacctcag gaagccccta gagaacctgg aatgaccga catgttcaga    900 cagtttcagg ctgacttcac gagtcttca gaccaagagc ctctccacgt cgcgcaggcg    960
ctgcagaaaa tgaagatcga ggtgaacgag agtggcacgg tggcctcctc atccacagct   1020
gtcatagtct cagcccgcat ggcccccgag gagatcatca tggacagacc cttcctcttt   1080
gtggtccggc acaaccccac aggaacagtc cttttcatgg gccaagtgat ggaaccctga   1140
```

<210> SEQ ID NO 13
<211> LENGTH: 19
<212> TYPE: DNA
<213> ORGANISM: Artificial Sequence
<220> FEATURE:
<223> OTHER INFORMATION: Synthetic primer

<400> SEQUENCE: 13
ggaattcaag gagctatgg                                                    19

<210> SEQ ID NO 14
<211> LENGTH: 23
<212> TYPE: DNA
<213> ORGANISM: Artificial Sequence
<220> FEATURE:
<223> OTHER INFORMATION: Synthetic primer

<400> SEQUENCE: 14
gctctagatt tccactggtg atg                                               23

<210> SEQ ID NO 15
<211> LENGTH: 26
<212> TYPE: DNA
<213> ORGANISM: Artificial Sequence
<220> FEATURE:
<223> OTHER INFORMATION: Synthetic primer

<400> SEQUENCE: 15
ggaattcatg gatgagatca gcacgg                                            26

<210> SEQ ID NO 16
<211> LENGTH: 24
<212> TYPE: DNA
<213> ORGANISM: Artificial Sequence
<220> FEATURE:
<223> OTHER INFORMATION: Synthetic primer

<400> SEQUENCE: 16
gctctagatt tccactggct gatg                                              24

<210> SEQ ID NO 17
<211> LENGTH: 34
<212> TYPE: DNA
<213> ORGANISM: Artificial Sequence
<220> FEATURE:
<223> OTHER INFORMATION: Synthetic primer

<400> SEQUENCE: 17
ggaattcatg cagttcaaga ttgaggagaa gggc                                   34

<210> SEQ ID NO 18
<211> LENGTH: 24
<212> TYPE: DNA
<213> ORGANISM: Artificial Sequence
<220> FEATURE:
<223> OTHER INFORMATION: Synthetic primer

<400> SEQUENCE: 18
gctctagatt tccactggct gatg                                              24

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
ggaattcaag gagctcatgg                                                   20

<210> SEQ ID NO 20
<211> LENGTH: 23
<212> TYPE: DNA
<213> ORGANISM: Artificial Sequence -continued

```
<220> FEATURE:
<223> OTHER INFORMATION: Synthetic primer

<400> SEQUENCE: 20
gctctagatc aaggctccat cac                                              23
```

METHODS FOR MODULATING ANGIOGENESIS

This application is a continuation-in-part application of U.S. patent application Ser. No. 10/506,225, filed Dec. 20, 2004, now issued as U.S. Pat. No. 7,241,446 which claims the benefit of priority from PCT/US2003/009981, filed Apr. 1, 2003, and U.S. Provisional Application Ser. Nos. 60/369,392, filed Apr. 1, 2002 and 60/448,301, filed Feb. 14, 2003, the contents of which are incorporated herein by reference in their entireties.

This invention was supported in part by funds from the U.S. government (NIH Grant Nos. RO1-HL59590 and R01 HL069948). Therefore, the U.S. government may have certain rights in this invention.

BACKGROUND OF THE INVENTION

Angiogenesis is the formation of new capillary blood vessels as outgrowths of pre-existing vessels. The tightly regulated process plays a vital role in many physiological processes, such as embryogenesis, wound healing and menstruation. Angiogenesis is also important in certain pathological events. In addition to a role in solid tumor growth and metastasis, other notable conditions with an angiogenic component are arthritis, psoriasis and diabetic retinopathy (Hanahan and Folkman (1996) *Cell* 86:353-364; Fidler and Ellis (1994) *Cell* 79(2):185-188).

At the onset of angiogenesis, the quiescent endothelium is destabilized into migratory, proliferative endothelial cells. The angiogenic (activated) endothelium is maintained primarily by positive regulatory molecules. In the absence of such molecules, the endothelium remains in a differentiated, quiescent state that is maintained by negative regulatory molecules, angiogenesis inhibitors (Bouck (1990) *Cancer Cells* 2:179-185; Hanahan and Folkman (1996) supra). Normally, the negative and positive activities are balanced to maintain the vascular endothelium in quiescence (Hanahan and Folkman (1996) supra; Folkman and Klagsbrum (1987) *Science* 235:442-447). A shift in the balance of the positive and negative regulatory molecules can alter the differentiated state of the endothelium from the non-angiogenic, quiescent to the angiogenic state (Hanahan and Folkman (1996) supra). In the switch to pro-angiogenesis, the quiescent endothelial cells are stimulated to migrate toward a chemotactic stimulus, lining up in a tube (sprout) formation (Folkman and Klagsbrum (1987) supra). These cells also secrete proteolytic enzymes that degrade the endothelial basement membrane, thus allowing the migrating endothelial cells to extend into the perivascular stroma to begin a new capillary sprout. The angiogenic process is characterized by increased proliferation of endothelial cells to form the extending capillary (Folkman and Klagsbrum (1987) supra; Moses, et al. (1995) *Int. Rev. Cytol.* 161:1-48; Martiny-Baron and Marme (1995) *Curr. Opin. Biotechnol.* 6:675-680; Liotta, et al. (1991) *Cell* 64:327-336).

Vascular endothelial growth factor (VEGF) is a mitogenic factor that stimulates pro-angiogenic properties, including endothelial cell migration and proliferation. VEGF induces the expression of plasminogen activator proteolytic pathway proteins that participate in cellular invasive and remodeling processes (Pepper, et al. (1991) *Biochem. Biophys. Res. Commun.* 181:902-906; Mandriota, et al. (1995) *J. Biol. Chem.* 270:9709-9716; Mignatti, et al. (1989) *J. Cell. Biol.* 108:671-682). VEGF-A RNA can undergo alternative splicing to produce four isoforms (Leung, et al. (1989) *Science* 246:1306-1309; Houck, et al. (1991) *Mol. Endocriniology* 5:1806-1814; Tischer, et al. (1991) *J. Biol. Chem.* 26611947-22954). Three of those isoforms, VEGF-$A_{165, 189, 206}$, bind to heparin. Pro-VEGF affinity for heparin appears to be important in the regulation of the availability of VEGF at the cell surface (Houck, et al. (1992) *J. Biol. Chem.* 267:26031-26037), where it can interact with its tyrosine kinase receptors to exert its activity (Gitay-Goren, et al. (1992) *J. Biol. Chem.* 267: 6093-6098). VEGF-A can be released from heparin in an inactive or active form (Ortega, et al. (1998) *Biol. Cell* 90:381-390). Plasmin and urokinase plasminogen activator (uPA) cleaves pro-VEGF into an active form of varied sizes depending upon the isoform and the activator molecule (Plouet, et al. (1997) *J. Biol. Chem.* 272:13390-13396).

There are naturally occurring molecules that serve as negative regulators of angiogenesis. Angiostatin, one such negative regulator, is a 38-45 kDa cleavage product of plasminogen, containing kringle domains 1-4 (K1-4) (O'Reilly, et al. (1994) *Cell* 79:315-328; O'Reilly, et al. (1996) *Nat. Med.* 2:689-692). Plasminogen, the precursor of plasmin, is activated when it is cleaved at the carboxy-terminus by plasminogen activators. The amino terminus contains five consecutive kringle domains, each approximately 9 kDa. The greatest inhibitory activity of angiostatin is contained within kringles 1-3 (Cao, et al. (1996) *J. Biol. Chem.* 271:29461-29467) and kringles 1-5 (Cao (1999) *Proc. Natl. Acad. Sci. USA* 6:5728-5733). The mechanism for angiostatin inhibition of endothelial cell growth in vitro and angiogenesis in vivo is unclear.

Plasminogen activator inhibitor-1 (PAI-1), a serpin family, serine protease inhibitor, is a multifunctional regulatory protein in the plasminogen activator proteolytic (Chapman, et al. (1982) *Cell* 28:653-662; Chapman (1997) *Curr. Opin. Cell Biol.* 9:714-724) and fibrinolytic pathways (Loskutoff and Curriden (1990) *Ann. NY Acad. Sci.* 598:238-247; Collen (1999) *Thromb. Haemost.* 82:258-270). Active PAI-1 (vitronectin-bound) inhibits proteolytic degradation of the extracellular matrix by inhibiting uPA/tPA, which in turn inhibits cell migration and invasion (Blasi (1999) *Thromb. Haemost.* 82:298-304). PAI-1 can exist in an active, inactive/latent or substrate-cleaved conformation (Lawrence, et al. (1997) *J. Biol. Chem.* 272:7676-7680; Debrock and Declerck (1998) *Thromb. Haemost.* 79:597-601). The PAI-1 reactive center loop (RCL), located at amino acids 320-351 (Schechter and Berger (1967) *Biochem. Biophys. Res. Commun.* 27:157-162; Laskowski and Kato (1980) *Annu. Rev. Biochem.* 49:593-626), initially interacts with uPA at Arg-346 (Lawrence, et al. (1994) *J. Biol. Chem.* 269:27657-27662; Tucker and Gerard (1996) *Eur. J. Biochem.* 237:180-187) to form a stable PAI-1/uPA complex to inactivate uPA (York, et al. (1991) *J. Biol. Chem.* 266:8495-8500). In the active/latent configuration of PAI-1 (not bound to vitronectin), the RCL spontaneously inserts into the β-sheet of strand 4a to stabilize the PAI-1 structure (Mottonen, et al. (1992) *Nature* 355:270-273; Egelund, et al. (1997) *Eur. J. Biochem.* 248:775-785; Kjoller, et al. (1996) *Eur. J. Biochem.* 241:38-46). It has been shown that when PAI-1 is cleaved between residues P and P' in the RCL, PAI-1 is converted to a substrate (Lawrence, et al. (1997) supra; Debrock and Declerck (1998) supra). In the cleaved conformation, the RCL is partially inserted into β-sheet of strand A, thus making the structure of cleaved and inactive PAI-1 more similar to each other than to active PAI-1. However, it has been demonstrated that there are distinct conformational differences between latent and cleaved PAI-1 (Sancho (1995) *Biochemistry* 34:1064-1069). The PAI-1 region distant from the RCL contains many binding domains for regulatory molecules involved in the proteolytic and fibrinolytic pathways. This region of PAI-1 has interactive sites for vitronectin (Lawrence, et al. (1994) supra; Padmanabhan and Sane (1995) *Thromb. Haemost.* 73:829-834; Van Meijer, et al. (1994) *FEBS Lett.* 352:342-346; Seiffert, et al. (1994) *J. Biol. Chem.* 269:2659-2666), heparin (Ehrlich, et al. (1992) *J. Biol. Chem.* 267:11606-11611), tPA, uPA (Keijer, et al. (1991) *Blood* 78:401-409; Reilly and Hutzelmann (1992) *J. Biol. Chem.* 267:17128-17135), thrombin (Ehrlich, et al. (1992) supra), and fibrin (Ehrlich, et al. (1992) supra; Reilly and Hutzelmann (1992) supra). Through its interactions with some of the same regulatory molecules in the proteolytic and fibrinolytic pathways, it has been demonstrated that PAI-1 (active and inactive) is also able to play a role in anti-angiogenic mechanisms (Mulligan-Kehoe, et al. (2001) *J. Biol. Chem.* 276:8588-8596; Schnaper, et al. (1995) *J. Cell Physiol.* 165:107-118; Stefansson, et al. (2001) *J. Biol. Chem.* 276:8135-8141).

A recent report demonstrates that when a truncated porcine PAI-1 protein rPAI-1$_{23}$, is incubated with plasminogen and uPA, it induces formation of an angiostatin-like protein that has proteolytic activity (Mulligan-Kehoe, et al. (2001) supra) . In this reaction, angiostatin is formed from cleaved plasmin. uPA enhances the formation of the angiostatin-like protein by increasing the amount of available plasmin. The proteolytic activity of the 36 kDa angiostatin is ultimately inhibited by increasing amounts of rPAI-1$_{23}$ that are available for binding uPA and/or plasminogen. In this second mechanism, rPAI-1$_{23}$ reduces the numbers of uPA/plasminogen interactions; thus, reducing the amount of plasmin produced. Cultured endothelial cells exposed to rPAI-1$_{23}$ exhibit a decrease in proliferation, increased apoptosis, and decreased migration in the presence of VEGF. This truncated PAI-1 appears to be exposing sites that participate in a functional role for PAI-1 in generating angiostatin fragments from plasmin.

Previously, zymographic analysis demonstrated the importance of rPAI-1$_{23}$ interactions with uPA, plasminogen, and plasmin that result in angiostatin formation. Furthermore, it has been shown that rPAI-1$_{23}$ blocks migration of VEGF-stimulated endothelial cells (Mulligan-Kehoe, et al. (2001) supra).

Anti-angiogenic tumor treatment strategies are based upon inhibiting the proliferation of budding vessels, generally at the periphery of a solid tumor. These therapies are often applied to reduce the risk of micrometastasis or to inhibit further growth of a solid tumor after more conventional intervention (such as surgery or chemotherapy).

The recognition of VEGF as a primary stimulus of angiogenesis in pathological conditions has led to various attempts to block VEGF activity. Inhibitory anti-VEGF receptor antibodies, soluble receptor constructs, antisense strategies, RNA aptamers against VEGF and low molecular weight VEGF receptor tyrosine kinase (RTK) inhibitors have all been proposed for use in interfering with VEGF signaling (Siemeister et al. (1998) *Cancer Metastasis Rev.,* 17(2):241-248). Monoclonal antibodies against VEGF have been shown to inhibit human tumor xenograft growth and ascites formation in mice (Kim, et al. (1993) *Nature* 362:841-844; Asano, et al. (1998) *Hybridoma* 17:185-90; Mesiano, et al. (1998) *Am. J. Pathol.* 153(4):1249-1256; Luo, et al. (1998) *Cancer Res.* 58(12): 2594-2600; Borgstrom, et al. (1996) *Prostate* 35(1) :1-10; Borgstrom, et al. (1998) *Anticancer Research* 19(5B):4203-11). Moreover, U.S. Pat. No. 6,342,221 discloses the use of anti-VEGF antibodies to specifically inhibit VEGF binding to the VEGFR-2 receptor.

Regulation of angiogenesis by PAI proteins has also been suggested. For example, U.S. Pat. No. 5,830,880 discloses the expression of PAI-1, PAI-2, PAI-3 and angiostatin through a gene therapy approach to inhibit angiogenesis. Furthermore, RCL mutants (residues 331-346) of PAI-1 have been disclosed in PCT Publication No. WO 97/39028 which are resistant to elastase inactivation and/or have a high affinity for vitronectin.

SUMMARY OF THE INVENTION

Angiogenesis is the process of blood vessel growth towards a tissue in need of oxygen or an injured tissue. Angiogenesis can be either harmful or beneficial, for example, in cases such as tumor growth, angiogenesis towards the tumor can supply the tumor with nutrients and support its growth, thus further harming the patient. However, in occlusive (clotting of blood vessels) diseases, the ability to spontaneously develop collateral vessels often determines the level of tissue viability. Thus, methods of stimulating or inhibiting angiogenic processes are needed. The present invention meets this need by providing recombinant PAI-1 proteins useful in stimulating or inhibiting angiogenesis.

In this regard, the present invention provides a method for modulating angiogenesis with a PAI-1 isoform. The method involves administering an effective amount of a PAI-1 isoform lacking the RCL domain and containing a complete heparin-binding domain or lacking at least a portion of the heparin-binding domain so that angiogenesis is modulated. In one embodiment, the PAI-1 isoform lacking both the RCL domain and at least a portion of the heparin-binding domain is useful in blocking or decreasing angiogenesis. In a preferred embodiment, a PAI-1 isoform for blocking or decreasing angiogenesis includes rPAI-1$_{23}$ and rPAI-1$_{A23}$. In another embodiment, the PAI-1 isoform lacking the RCL domain and containing a complete heparin-binding domain is useful in stimulating or increasing angiogenesis. In a particular embodiment, a PAI-1 isoform for increasing or stimulating angiogenesis includes rPAI-1$_{Hep23}$. In a further embodiment, the PAI-1 isoform lacking the RCL domain and at least a portion of the heparin-binding domain is useful to block the release of VEGF from a VEGF-heparin complex thereby blocking angiogenesis. In another preferred embodiment of the present invention, the PAI-1 isoform for blocking the release of VEGF includes rPAI-1$_{23}$.

The present invention also includes methods for stimulating apoptosis or reducing cell proliferation or migration. These methods involve administering an effective amount of a PAI-1 isofrom which lacks both the RCL and heparin-binding domains. In a particular embodiment, a PAI-1 isoform for stimulating apoptosis or reducing cell proliferation or migration includes rPAI-1$_{A23}$. A method for stimulating plaque regression is also provided. In accordance with this method of the invention, an effective amount of an anti-angiogenic PAI-1 isoform lacking an RCL domain and lacking at least a portion of a heparin-binding domain is administered to a subject thereby stimulating plaque regression.

The present invention is also a method for modulating angiostatin formation. The method involves administering a PAI-1 isoform which lacks an RCL domain and lacks at least a portion of a heparin-binding domain so that angiostatin containing kringle 1-3 or kringle 1-4 is formed. In a particular embodiment, a PAI-1 isoform for modulating angiostatin formation includes rPAI-1$_{23}$ and rPAI-1$_{A23}$.

A method of treating an angiogenesis-mediated disease is embraced by the present invention. The method involves administering either a proangiogenic or anti-angiogenic isoform of PAI-1 so that the signs or symptoms of an angiogenesis-mediated disease are reduced. In one embodiment, an anti-angiogenic PAI-1 isoform lacks an RCL domain and lacks at least a portion of a heparin-binding domain. In accordance with this embodiment, the anti-angiogenic PAI-1 isoform is rPAI-1$_{23}$ or rPAI-1$_{A23}$. In still another embodiment, a proagiogenic PAI-1 isoform lacks an RCL domain and contains a complete heparin-binding domain. In accordance with this embodiment, the proangiogenic PAI-1 isoform is rPAI-1$_{Hep23}$.

DETAILED DESCRIPTION OF THE INVENTION

Figure 1:
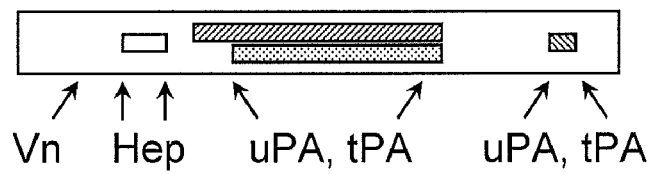
FIG. 1 illustrates rPAI-1 truncations relative to the human and porcine proteins. The domains that interact with specific molecules in the proteolytic, fibrinolytic and adhesion processes are indicated with arrows and bars. Overlapping domains are indicated. Deletions were based on the alignment of the human and porcine genes.
Figure 1:
Figure 1:
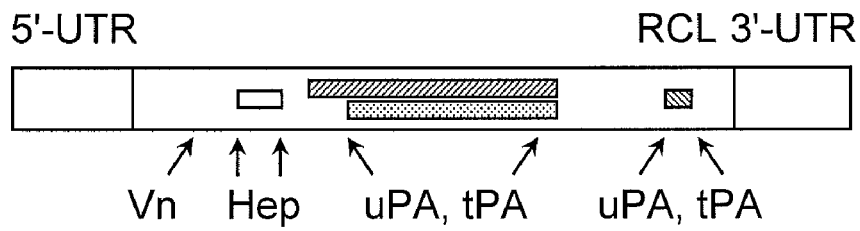
Figure 1:
Figure 1:
Figure 1:
Figure 1:
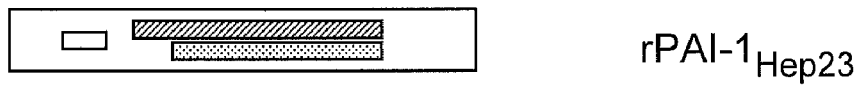

The present invention provides methods of modulating angiogenesis through recombinant PAI-1 (rPAI-1) protein interactions. Four isoforms of rPAI-1 were generated, with and without the heparin-binding domain and the reactive center loop (FIG. 1, Table 1), and used to demonstrate the function of PAI-1.

TABLE 1

| Isoform | Heparin-Binding Domain | RCL Domain | Human SEQ ID NO: | Porcine SEQ ID NO: |
|---|---|---|---|---|
| rPAI-1$_{Hep23}$ | Not deleted | Deleted | 1 | 5 |
| rPAI-1$_{24}$ | Partial Deletion | Not Deleted | 2 | 6 |
| rPAI-1$_{A23}$ | Deleted | Deleted | 3 | 7 |
| rPAI-1$_{23}$ | Partial Deletion | Deleted | 4 | 8 |

There are no known functional differences between human (huPAI-1) and porcine PAI-1 (poPAI-1) (Bijnens, et al. ((1997) Thromb. Haemost. 77:350-356; Bosma, et al. (1988) J. Biol. Chem. 263:9129-9141). As such, particular embodiments embrace proteins of human (SEQ ID NOs:1-4) or porcine (SEQ ID NO:5-8) origin or a protein sharing 90 or 95% sequence identity with a human or porcine protein disclosed herein. Two of the rPAI-1 proteins, rPAI-1$_{Hep23}$ and rPAI-1$_{A23}$ are encoded by DNA sequence identical to the rPAI-1$_{23}$ (Mulligan-Kehoe, et al. (2001) supra) except that rPAI-1$_{Hep23}$ contains the codons for the entire heparin-binding domain, which have been completely deleted in rPAI-1$_{A23}$, and 21 additional amino acid residues at the N-terminus (Met-Gln-Phe-Lys-Ile-Glu-Glu-Lys-Gly-Met-Ala-Pro-Ala-Leu-Arg-Gln-Leu-Tyr-Lys-Glu-Leu-Met-Gly-Pro-Trp-Asn-Lys; SEQ ID NO:9). The rPAI-1$_{24}$ was the only rPAI-1 isoform that contained the reactive center loop (RCL) on the carboxyl terminus (amino acids 320-351). Amino acid residues 262-379 in mature poPAI-1 were deleted from the carboxyl termini of rPAI-1$_{23}$, rPAI-1$_{Hep23}$, and rPAI-1$_{A23}$. The RCL was within the deleted region and, therefore, enabled examination of the importance of an uPA site at residues 128-145, in the absence of the primary uPA site at Arg-346. The heparin-binding domain corresponding to amino acid residues 65-88 (Lys-Ile-Glu-Glu-Lys-Gly-Met-Ala-Pro-Ala-Leu-Arg-Gln-Leu-Tyr-Lys-Glu-Leu-Met-Gly-Pro-Trp-Asn-Lys; SEQ ID NO:10) was completely deleted in the rPAI-1$_{A23}$ isoform. The heparin-binding domain of rPAI-1$_{23}$ lacked amino acid residues 65-82.

Various experimental approaches were used to demonstrate the impact that the four rPAI-1 isoforms had on angiogenic processes. For example, rPAI-1 protein interactions with heparin, uPA and plasminogen were examined. Furthermore, in vitro angiogenic activity of the rPAI-1 proteins was analyzed through apoptosis, cell proliferation and migration experiments. Moreover, the interactions of a VEGF-heparin complex with rPAI-1 proteins, uPA, and plasmin were determined and the effect on VEGF activation in rPAI-1-treated cells was examined.

Protease activity was measured in reconstitution reactions combining recombinant, truncated rPAI-1 molecules with uPA and plasminogen with and without heparin. Zymographic analysis indicated that three of the four truncated PAI-1 proteins in combination with uPA and plasminogen resulted in the production of proteolytic fragments that migrated at 34-38 kDa. The rPAI-1$_{23}$ protein induced formation of two 34-38 kDa proteolytic angiostatin fragments from plasmin. However, the rPAI-1$_{A23}$ and rPAI-1$_{24}$ proteins each had a single band that corresponded to one of the 34-38 kDa fragments visualized in the rPAI-1$_{23}$ products. In the case of rPAI-1$_{A23}$, a proteolytic band appeared at or near the size of the lower proteolytic fragment induced by rPAI-1$_{23}$ cleavage of plasmin. The rPAI-1$_{24}$ protein induced a proteolytic fragment at or near the molecular mass corresponding to the larger of the two plasmin cleavage products induced by rPAI-1$_{23}$. The rPAI-1$_{Hep23}$ did not produce a proteolytic fragment at 34-38 kDa. The rPAI-1$_{23}$ protein (partial heparin-binding domain) maintained its activity when bound to heparin. Similarly, the proteolytic activity associated with a reaction mix containing uPA, plasminogen, and rPAI-1$_{Hep23}$ (complete heparin domain) was not altered in the presence of heparin. The rPAI-1$_{A23}$ protein (lacking a heparin-binding domain) and the rPAI-1$_{24}$ protein (containing the RCL and a partial heparin domain) did not demonstrate proteolytic plasmin cleavage products when incubated with heparin. The proteolytic proteins near 80 kDa corresponded to plasmin. Proteolytic proteins near 50 kDa may represent a different plasmin cleavage product containing a greater number of plasminogen kringle domains. The function of the rPAI-1$_{Hep23}$ isoform (complete heparin domain) in a reaction with uPA and plasminogen as compared with rPAI-1$_{23}$ isoform (partial heparin-binding domain) showed that binding to heparin did not alter the inability of rPAI-1$_{Hep23}$ to mediate the formation of proteolytic fragments at a molecular mass near 34 kDa. These experiments showed that a full heparin-binding domain may block the ability of PAI-1 to induce proteolytic proteins corresponding to or near the molecular mass of antiostatin containing K1-3.

In vitro analyses of angiostatin production following rPAI-1 treatment zymography analysis of proteolytic angiostatin in culture medium of rPAI-1-treated endothelial cells was conducted. The zymography analysis of the culture medium from rPAI-1$_{23}$-treated bovine aortic endothelial cells (BAEC) did not show proteolytic angiostatin at any of the examined time points (6, 15, 24, 36, 48, and 72 hours). On the other hand, the medium from the rPAI-1$_{A23}$-treated cells contained a substantial amount of proteolytic activity near 34 kDa in all of the examined time points. Analysis of the extracellular matrix proteins showed that proteolytic angiostatin was produced after 72 hours of rPAI-1$_{23}$ or rPAI-1$_{A23}$ treatment. The molecular mass of the proteolytic fragment in rPAI-1$_{A23}$-treated cells corresponded to the molecular mass that has been shown to contain angiostatin kringles 1-3 (Mulligan-Kehoe, et al. (2001) supra; Mulligan-Kehoe, et al. (1991) supra) . The results indicate that rPAI-1$_{A23}$ is more efficient than rPAI-1$_{23}$ in producing proteolytic angiostatin in BAEC.

To further demonstrate that the plasminogen (plasmin) cleavage products formed in reconstitution reactions containing rPAI-1 proteins, uPA and plasminogen contained kringle domains 1-3, nitrocellulose membranes of said cleavage products were probed with anti-kringle 1-3 (angiostatin) antibodies. Samples containing 3, 15 or 30 nM of rPAI-1$_{23}$ had fragments containing kringles 1-3 at a molecular mass corresponding to the size that was visualized by zymography. Additionally, there were fragments containing kringles 1-3 at a molecular mass near 45 kDa that correspond to the reported size of kringles 1-4, and 70-80 kDa that correspond to the size of plasmin. The reaction product of 15 nM of rPAI-1$_{A23}$, uPA and plasminogen contained angiostatin kringles 1-3 at 34-36 kDa. However, that fragment was absent when 3 or 30 nM of rPAI-1$_{A23}$ were part of the reaction with uPA and plasminogen. In the reactions containing either rPAI-1$_{24}$ or rPAI-1$_{A23}$, plasminogen kringles 1-3 were not present at 34-36 kDa. There were detectable fragments containing kringles 1-3 near 45 kDa in the reactions containing 3 nM of rPAI-1$_{24}$. These data showed that the reaction of uPA and plasminogen with all concentrations of rPAI-1$_{23}$ resulted in the formation of plasminogen kringles 1-3 (angiostatin) at 34-36 kDa, which is consistent with the molecular mass of the proteolytic fragments observed on the zymogram. Additionally, there is a greater amount of kringles 1-3 at 45 kDa which is representative of a less potent angiostatin.

Immunoblot analyses of angiostatin in culture medium of rPAI-1-treated endothelial cells was also conducted. The results of the immunoblot analysis of the culture medium protein isolated from rPAI-1 treated or untreated BAEC showed that, at all three time points (24, 36, and 48 hours) and in all three test samples (no treatment, rPAI-1$_{23}$-treated, and rPAI-1$_{A23}$-treated), there were predominant proteins containing angiostatin kringles 1-3 at a molecular weight between 34 and 50 kDa and a less predominant fragment at 28 kDa. The kringles 1-3 fragments near 50 kDa were less intense in the rPAI-1$_{A23}$ samples at 24 hours, but they became more intense at each later time point. The rPAI-1$_{A23}$ samples at 36 and 48 hours displayed a pronounced K1-3 fragment between 28 and 34 kDa. In the 36 and 48 hour rPAI-1$_{23}$-treated cells, there was an additional processed/cleaved kringles 1-3 fragment beneath the fragment observed between 34 and 50 kDa. The 36 and 48 hour untreated samples did not contain additional cleavage products. The data from these experiments demonstrate that in rPAI-1$_{A23}$-treated cells at 36 and 48 hours, the fragments containing kringles 1-3 have undergone additional processing to result in angiostatin of a lower molecular mass; a size of angiostatin with greater anti-angiogenic activity (O'Reilly, et al. (1994) supra; Lucas, et al. (2000) *Biochemistry* 39:508-515; Cao, et al. (1999) supra; and O'Reilly, et al. (1996) supra) . The amount of angiostatin is clearly in greater abundance in rPAI-1$_{A23}$-treated cells.

The results provided herein indicated that rPAI-1$_{23}$ may preferentially cleave plasminogen into angiostatin while rPAI-1$_{A23}$ may cleave plasmin into angiostatin with associated proteolytic activity. Thus, further analysis of angiostatin produced in biochemical reactions containing rPAI-1 proteins was performed wherein angiostatin was produced in varied permutations with rPAI-1 and uPA. This analysis provided a more extensive examination of the plasminogen/plasmin cleavage products in reactions containing either rPAI-1$_{23}$ or rPAI-1$_{A23}$ and two-chain uPA (tcuPA). Immunoblots, containing the products of the biochemical reactions, probed for angiostatin kringles 1-3, kringle 4, and mini-plasminogen were examined. In these reactions, the rPAI-1 protein was first reacted with 0.25 IU of tcuPA before adding 1 IU of plasminogen. The rPAI-1$_{23}$ samples contained kringles 1-3 (K1-3) at 28-34 kDa, 45 kDa, 50 kDa, and near 70 kDa. The intensity of the 34 kDa fragment increased with increasing concentrations of rPAI-1$_{23}$. At the highest concentration of rPAI-1$_{23}$ (30 nM), the 45 kDa K1-3 fragment was reduced and there was also a decrease in the 70 kDa fragment. In reactions containing rPAI-1$_{A23}$, the 24-28 kDa K1-3 fragments were only present when rPAI-1$_{A23}$ was at 15 nM. There were changes in the intensity of the fragments containing K1-3 at 45 and 50 kDa, which also appeared to be shifting upward. The intensity of plasmin at 70 kDa was not reduced in samples where the K1-3 fragments were increased.

When the same reactions were probed for kringle 4 (K4), there was a scant amount of K4 near 50 kDa in the reactions containing higher concentrations of rPAI-1$_{23}$ (15 and 30 nM)) and rPAI-1$_{A23}$. The greatest intensity was in the reaction which contained 15 nM of rPAI-1$_{A23}$. In the rPAI-1$_{A23}$ samples, there were two fragments near 45-50 kDa. There was not any detectable plasmin or plasminogen at 70-80 kDa in the reactions containing rPAI-1$_{23}$, but they were detectable in the rPAI-1$_{A23}$ samples. A mini-plasminogen (MP) probe of the reaction mixtures did not detect any fragments below 70 kDa and MP was only visible at levels slightly above background near 70 kDa.

Reaction mixtures were then probed for K1-3, K4, and MP in a permutation where uPA, plasminogen, and either rPAI-1$_{23}$ or rPAI-1$_{A23}$ were added simultaneously. In the K1-3-probed reactions containing rPAI-1$_{23}$, the K1-3 fragments at 28-34 kDa were nearly undetectable, the 45 and 50 kDa fragments in the samples containing 3 and 15 nM of rPAI-1$_{23}$ were intense, and intense K1-3 protein at 70-80 kDa was present at all concentrations of rPAI-1$_{23}$ (3, 15, and 30 nM). The reactions rPAI-1$_{A23}$ showed a dramatic difference in K1-3 fragments as compared to the rPAI-1$_{23}$ samples. The rPAI-1$_{A23}$ samples all displayed a distinct 28-34 kDa fragment. A less intense doublet near 45 kDa was visualized in samples containing 3 and 15 nM of rPAI-1$_{A23}$. The 50 and 70-80 kDa fragments were absent at all three concentrations of rPAI-1$_{A23}$ (3, 15, and 30 nM).

A K4 probe of the same reaction permutation containing rPAI-1$_{23}$ revealed the presence of angiostatin fragments near 45 kDa at all three concentrations of rPAI-1$_{23}$; a slight angiostatin fragment at 50 kDa in reactions containing 3 and 15 nM of rPAI-1$_{23}$; and K4 was not detectable near 70-80 kDa when rPAI-1$_{23}$ was present at 15 and 30 nM. A mini-plasminogen probe of the reaction mixture showed a fragment at 34 kDa when rPAI-1$_{23}$ was present at 15 and 30 nM. The MP fragment was of a slightly smaller molecular mass than the K4 probed fragments. The sample reaction mixtures containing rPAI-1$_{A23}$ did not reveal any detectable K4 or mini-plasminogen in this permutation.

The immunoblots indicated that there were differences in angiostatin produced in reactions with rPAI-1$_{23}$ and rPAI-1$_{A23}$. The differences were not only due to structural differences in rPAI-1, but were, also in part, due to molecular interactions that seemingly occurred in response to exposed domains in rPAI-1$_{23}$ and rPAI-1$_{A23}$. The alteration in angiostatin fragments containing K1-3 indicated that at high concentrations of rPAI-1$_{A23}$, which exceeded a 1:1 molar ratio with uPA, plasminogen was cleaved into angiostatin fragments near 34 kDa. However, in the permutation where all three molecules were allowed to interact simultaneously, the cleavage product was angiostatin containing K1-4 near 45 kDa. When rPAI-1$_{23}$ was in excess, then the K1-3 fragments at 50 and 45 kDa diminished in intensity. These data show that a fragment containing kringles 1-4 was the preferred cleavage product in a reaction where uPA first reacted with rPAI-1$_{A23}$ before plasminogen was added. When rPAI-1$_{A23}$, uPA and plasminogen were simultaneously added to a reaction, two sets of angiostatin fragments containing K1-3 were produced. While it appeared that the 34 kDa fragment was more abundant, there may have been two cleavage products at the onset or the K1-4 product may have underwent additional cleavage/processing to 34 kDa as rPAI-1$_{A23}$ concentrations were was increased. The significant difference in these reactions, when compared to the permutation where uPA was first reacted with rPAI-1$_{A23}$ before adding plasminogen, was the complete loss of plasmin and/or plasminogen. These collective data indicate that both rPAI-1$_{23}$ and rPAI-1$_{A23}$ may bind uPA and/or plasminogen and the varied interactions alter the cleavage site in plasminogen and/or plasmin.

As the data indicated that rPAI-1$_{23}$ and rPAI-1$_{A23}$ may cleave plasminogen, additional biochemical reactions were performed to analyze interactions of rPAI-1 with plasminogen. Increasing concentrations of rPAI-1$_{23}$ and rPAI-1$_{A23}$ were each incubated with plasminogen (without uPA) and then immunoblots containing each reaction mixture were probed for mini-plasminogen. The probed immunoblots revealed a distinct plasminogen cleavage product near 50 kDa in all reactions containing the rPAI-1$_{23}$ protein (3, 15 and 30 nM). In the same reactions, a corresponding decrease in plasminogen at 80 kDa was seen as well, clearly demonstrating that plasminogen was cleaved into the smaller product. In contrast, the rPAI-1$_{A23}$ protein did not cleave plasminogen, even when increasing concentrations of the recombinant protein were added. Based on the mini-plasminogen antibody recognition, the 50 kDa cleavage product contained either multiple kringle domains to include K5 or a combination of kringle domains and the serine protease domain. The data demonstrates that the rPAI-1$_{23}$ recombinant protein cleaves plasminogen, while the rPAI-1$_{A23}$ protein does not.

To evaluate which cleavage products in reactions containing rPAI-1$_{23}$ resulted from plasminogen vs. plasmin, the cleavage products in a reaction containing rPAI-1$_{23}$ and plasminogen were examined. Additionally, the effect that uPA may potentially have on rPAI-1$_{23}$ cleavage of plasminogen was examined. These experiments showed distinct rPAI-1-cleaved plasminogen fragments containing K1-3 at 50 kDa, between 28-34 kDa, and predominantly at 45 kDa. These data demonstrate that the 28-34 kDa angiostatin was K1-3 cleaved from plasminogen. As increasing concentrations of uPA were added to the rPAI-1$_{23}$-plasminogen complex, the K1-3 at 28-34 kDa diminished and was eventually undetectable. This showed that uPA was able to compete rPAI-1$_{23}$ away from plasminogen in a uPA dose-dependent manner. A decrease in the amount of plasmin at 72 kDa was seen as compared to the plasmin formed in a uPA and plasminogen reaction. The results of these experiments indicated that rPAI-1$_{23}$ cleaved plasminogen into angiostatin K1-3, a more potent angiostatin fragment (Cao, et al. (1996) supra); uPA could reverse that cleavage by competing rPAI-1$_{23}$ away from plasminogen; and rPAI-1$_{A23}$ does not cleave plasminogen. These results further indicate that the rPAI-1$_{23}$ protein has both binding capabilities which have the potential to ultimately regulate plasmin formation.

Results provided herein demonstrated rPAI-1$_{A23}$ did not cleave plasminogen, however the effect that uPA may have on the formation of angiostatin was not investigated in reactions containing rPAI-1$_{A23}$ and plasminogen. Therefore, analysis of angiostatin in biochemical reactions containing rPAI-1$_{A23}$, uPA and plasminogen was performed. As K4 and MP were not identified in reactions where rPAI-1$_{A23}$, uPA, and plasminogen were added simultaneously to a reaction, concentrations of plasminogen were increased to 2 IU in the next series of experiments where uPA and rPAI-1$_{A23}$ concentrations were varied. Biochemical reactions, containing rPAI-1$_{A23}$, uPA and plasminogen, were performed to identify differences in angiostatin production that may occur as a result of the order in which the molecules were added to the reaction mixture.

Immunoblots of products of a reaction where all three reactants were added simultaneously, then incubated at 37° C. for two hours showed two distinct subsets of proteins containing K1-3. One subset had a molecular mass of approximately 45 kDa, the size reported for angiostatin K1-4 (O'Reilly, et al. (1994) supra, Cao, et al. (1996) supra). The other subset of protein fragments had a molecular mass between 28 and 36 kDa, the size reported for angiostatin K1-3 (O'Reilly, et al. (1994) supra, Cao, et al. (1996) supra) . The most observable differences in the two subsets of fragments containing K1-3 were the following. 1) The intensity of the 28-36 kDa protein fragments was greater than the 45 kDa fragments. 2) The intensity of the fragments near 45 kDa decreased as the concentration of rPAI-1$_{A23}$ was increased; as the uPA concentration was increased, the intensity of the 45 kDa fragments increased, but not to the level observed when rPAI-1$_{A23}$ was at the lowest concentration (3 nM) . 3) As the concentration of rPAI-1$_{A23}$ was increased, there was a shift in the molecular mass of both subsets of fragments containing K1-3; the shift was greater when uPA was at lower concentrations, which indicated that an increase in uPA stabilized the reaction and the site of plasminogen/plasmin cleavage. Alternatively, uPA may be in sufficient quantity to eliminate competition between rPAI-1$_{A23}$ and plasminogen for uPA binding sites. 4) There were differences in the amount of plasmin or plasminogen that remained uncleaved when rPAI-1$_{A23}$ was part of the reaction. In reactions where uPA was at the highest concentration (0.25 Units), plasmin and plasminogen were not detectable. When uPA was reduced by one-fourth, greater amounts of plasmin and plasminogen remained uncleaved. These observations indicated that uPA was bound to rPAI-1$_{A23}$ when the rPAI-1$_{A23}$ was in excess, such that uPA was unavailable to cleave plasminogen to form plasmin.

Further analysis of the interaction of tcuPA with rPAI-1$_{A23}$ was conducted to determine if this interaction stabilized the cleavage of plasmin or plasminogen into angiostatin. The results of immunoblots of biochemical reactions in which rPAI-1$_{A23}$ and uPA were first reacted before adding plasminogen showed stabilized angiostatin fragments in two distinct subsets of fragments: one subset near 50 kDa and the other subset at 34 kDa. The intensity of the fragment near 50 kDa decreased with increasing amounts of rPAI-1$_{A23}$. The plasmin remaining in the reaction mixtures was undetectable at the higher concentrations of rPAI-1$_{A23}$, independent of the uPA concentration. Differences between the results of these experiments and those provided above were that the molecular mass of the angiostatin fragments did not shift when rPAI-1$_{A23}$ and uPA were reacted first before adding plasminogen, which indicated that the interaction between uPA and rPAI-1$_{A23}$ stabilized the cleavage of plasmin.

Results provided herein indicate a competition between rPAI-1$_{A23}$ and plasminogen for binding uPA to result in a fraction of uncleaved plasmin or plasminogen. Thus, plasmin was made in a reaction containing uPA and plasminogen before adding rPAI-1$_{A23}$. In these reactions, the two subsets of angiostatin fragments were produced. The angiostatin fragments shifted slightly upward when the concentration of rPAI-1$_{A23}$ was increased. There was a diminution in both subsets of the angiostatin fragments when 30 nM of rPAI-1$_{A23}$ was in the reaction mix. The proteins corresponding to the molecular mass of plasmin were absent when low concentrations of uPA were combined with middle concentrations of rPAI-1$_{A23}$ (15 nM) and when both uPA and rPAI-1$_{A23}$ were at their highest concentrations (0.25 Units and 30 nM, respectively). There was a greater intensity in plasminogen when the reactions contained the highest concentration rPAI-1$_{A23}$ (30 nM) and the low and mid concentrations of uPA (0.025 and 0.05 Units). Those same reactions also contained less angiostatin at 45 and 28-36 kDa, which indicated that: uPA conversion of plasminogen into plasmin was not exhausted after 1 hour, and that rPAI-1$_{A23}$ was unable to cleave the residual plasminogen; increasing concentrations of rPAI-1$_{A23}$ were able to compete with plasminogen for binding to uPA to result in a reduction in plasmin levels; or rPAI-1$_{A23}$ can bind a uPA/plasminogen complex, alter the conformation of uPA or plasminogen to result in inefficient conversion of plasminogen into plasmin or a reduction in epitope binding by the antibody.

The reaction mixtures, containing rPAI-1$_{A23}$, uPA and plasminogen reacted in varied permutations, were also probed for plasminogen K4. K4 was present at 45 kDa in all reactions where uPA was first reacted with rPAI-1$_{A23}$ before adding plasminogen. The intensity of the fragments at 45 kDa decreased when the rPAI-1$_{A23}$ concentration was increased and uPA was at low and mid concentrations. At the highest concentration of uPA (0.25 Units), the intensity of the fragments containing K4 declined at all concentrations of rPAI-1$_{A23}$ (3, 15, and 30 nM). Additionally, when plasmin was first made (uPA+plasminogen) before adding rPAI-1$_{A23}$, K4 was detectable at the 45 kDa range when rPAI-1$_{A23}$ was at low and mid concentrations (3 and 15 nM), but was absent when rPAI-1$_{A23}$ was at the high concentration (30 nM). There was a slight shift in the angiostatin K1-4 fragment as the uPA concentration was increased. When all three reactants were simultaneously added to the reaction mixture and the resulting reaction products were probed for plasminogen K4, there was very little evidence of kringle 4. It was slightly detectable at 45 kDa when rPAI-1$_{A23}$ was at the lowest concentration, but was not detectable at 28-38 kDa. These data indicated that the binding domain for K4 was unavailable in most of the reaction mixtures.

None of the reactions containing rPAI-1$_{A23}$ showed K4 at the molecular mass corresponding to plasminogen or plasmin. The subset of angiostatin fragments at 28-36 kDa was not present when probed for K4 thus providing verification that the 28-36 kDa was K1-3 and not K1-4. There was no evidence of K1-4 in the reaction mixtures where uPA and plasminogen were first reacted before 30 nM of rPAI-1$_{A23}$ was added. In these same samples, K1-3 were diminished at 45 kDa and 28-34 kDa. These combined data indicate that there was a conformational change in plasminogen and/or plasmin in both permutations, which made the epitopes for K1-3 and K4 less available and unavailable, respectively.

Plasminogen fragments were undetectable on immunoblots, containing plasminogen, uPA and rPAI-1$_{A23}$ reaction mixtures in all permutations, which were probed for miniplasmin (K5+the serine protease domain).

Collectively these data demonstrate that in reactions with uPA and plasminogen, the rPAI-1$_{A23}$ protein is responsible for the cleavage of plasmin into angiostatin K1-3 at 28-36 kDa and angiostatin K1-4 at 45 kDa. Plasminogen remained in the reactions containing 30 nM of rPAI-1$_{A23}$; thus validating the results which showed that rPAI-1$_{A23}$ was unable to cleave plasminogen. Increasing concentrations of uPA along with increasing concentrations of rPAI-1$_{A23}$ appear to reduce uPA interactions with plasminogen, which was further evidenced by a decrease in plasmin cleavage products. The order in which the reactants were added appeared to alter the cleavage site in plasmin or plasminogen. In the biochemical reactions, an rPAI-1$_{A23}$, uPA complex stabilized the cleavage of plasmin into angiostatin K1-3 and K1-4.

The collective data indicated that tcuPA binds rPAI-1$_{A23}$. Therefore, experiments were performed to examine the interactions of rPAI-1$_{23}$ and rPAI-1$_{A23}$ with scuPA and tcuPA. Single-chain uPA was able to undergo a small degree of autocleavage, which was visible in the control scuPA as a fraction of tcuPA near 34 kDa. The data showed that when either rPAI-1$_{23}$ or rPAI-1$_{A23}$ were reacted with scuPA, there was a decrease in the amount of detectable scuPA and tcuPA as each rPAI-1 protein concentration was increased. These results indicated that both rPAI-1$_{23}$ and rPAI-1$_{A23}$ bind scuPA. As the concentration of rPAI-1 was increased, the binding interactions with uPA altered the conformation of uPA such that the epitope was not recognized by the antibody. When 30 nM of rPAI-1$_{A23}$ were reacted with scuPA, there was a substantial upward shift in the molecular mass of scuPA. Since the reacted proteins were electrophoresed on an SDS, non-reducing polyacrylamide gel, these data indicate that a covalent bond was formed between the two proteins.

The rPAI-1 proteins were also reacted with tcuPA and the reaction mix was probed for uPA. There was a slight upward shift in the molecular mass of tcuPA that had been reacted with plasminogen, 3 nM rPAI-1$_{23}$, and 3 nM rPAI-1$_{A23}$. There was a dramatic shift in tcuPA (from near 34 kDa to greater than 52 kDa) when it was reacted with 15 and 30 nM of rPAI-1$_{23}$. There was also a significant, but less consistent upward shift in the molecular mass of tcuPA reacted with 15 and 30 nM of rPAI-1$_{A23}$. The shift in the molecular mass of tcuPA indicated that both rPAI-1$_{23}$ and rPAI-1$_{A23}$ bound tcuPA and that a covalent bond was formed in the binding interactions to account for the obvious shift in mass.

Angiostatin production was examined when rPAI-1$_{A23}$ and rPAI-1$_{23}$ were added simultaneously to a reaction mixture with plasminogen and either scuPA or tcuPA. Immunoblots containing the products of the reactions were probed for angiostatin K1-3. When scuPA, rPAI-1$_{23}$, and plasminogen were added simultaneously to a reaction mixture, K1-3 were present as two distinct fragments between 34 and 50 kDa and less pronounced near 28 kDa. It appeared that the cleavage product was predominantly from plasmin. There was a slight, subtle upward shift in the molecular mass of the angiostatin fragments produced in a reaction with rPAI-1$_{23}$, tcuPA, and plasminogen. In these reactions, the angiostatin fragments were predominantly plasmin cleavage products as evidenced by the depletion in plasmin near 70 kDa. Alternatively, rPAI-1$_{23}$ may preferentially cleave plasminogen and/or bind uPA to inhibit plasmin formation altogether.

When rPAI-1$_{A23}$ was incubated with tcuPA and plasminogen, angiostatin fragments were observed near 45 kDa and between 28-34 kDa; plasmin and plasminogen were undetectable at 70-80 kDa. As the concentration of rPAI-1$_{A23}$ was increased, there was a reduction in the angiostatin fragments at 45 kDa. However, when scuPA was substituted for tcuPA, the same angiostatin fragments were present, but they were shifted upward with increasing concentrations of rPAI-1$_{A23}$. When rPAI-1$_{A23}$ was present at 30 nM, the kringle fragments were not present and plasminogen shifted to a molecular mass that exceeded the plasminogen control. Thus, uPA may have preferentially interacted with plasminogen to produce plasmin, which was then completely cleaved by rPAI-1$_{A23}$ or the complex that was formed with 30 nM of rPAI-1$_{A23}$ prevented plasmin formation and subsequent cleavage. This was evidenced biochemically by a shift in the molecular mass of plasminogen. These results demonstrate that both tcuPA and scuPA have the potential to substantially effect rPAI-1$_{A23}$-induced cleavage of plasmin into angiostatin. However, differences in the uPA conformation, that was scuPA versus tduPA, seemingly had an effect on angiostatin processing (additional cleavage) in reactions containing rPAI-1$_{23}$. Nevertheless, in all cases, plasmin levels were depleted.

To further analyze the nature of the 34 kDa proteolytic plasminogen product identified herein, biochemical experiments were conducted to analyze the plasminogen cleavage kinetics in reactions containing rPAI-1$_{23}$ and plasminogen. An rPAI-1$_{23}$ and plasminogen reaction mixture was equally distributed to multiple tubes so that uPA could be added at 15, 30, 45 and 60 minutes after the rPAI-1$_{23}$ and plasminogen reaction was initiated at 37° C. The reaction was stopped 2 hours after initiation of the incubation of the first samples (plasminogen and rPAI-1$_{23}$+plasminogen). Accordingly, the formation of the truncated proteolytic plasminogen product near 34 kDa and the cleavage of plasminogen by rPAI-1$_{23}$ was observed. Proteolytic proteins produced in the reactions were evaluated by zymography on a 15% SDS non-reducing polyacrylamide gel containing 1.3% casein. The reaction mixtures were electrophoresed on 4-20% gradient SDS, non-denaturing polyacrylamide gels. The transferred proteins were probed with an antibody specific for mini-plasmin (kringle 5+ the serine protease domain) to analyze plasminogen cleavage products that contained the protease domain.

Zymogram analysis clearly demonstrated that two proteolytic fragments were present near 34 kDa only in reactions where uPA was added to reaction mixtures containing plasminogen and rPAI-1$_{23}$. In these same reactions, there were additional proteolytic fragments with less activity near 50 kDa and 80 kDa (the molecular mass of intact plasmin). The amount of intact plasmin increased when uPA was added to the reaction. Concurrently, proteolytic proteins at 50 and 34 kDa increased as well. The intensity of proteolytic activity near 34 kDa was much greater when uPA was reacted with the rPAI-1$_{23}$ and plasminogen reaction mixture for 45 minutes as compared to shorter times with uPA in the mixture. In plasminogen and uPA reactions, in the absence of rPAI-1$_{23}$, intact plasmin near 80 kDa was not apparent until 60 minutes of incubation at 37° C.

The same reaction mixtures were analyzed for plasminogen mini plasmin by immunoblot analysis. Plasminogen cleavage products binding the anti-mini-plasmin antibody were identified near 50 kDa and 34 kDa, corresponding in molecular mass to the proteolytic proteins produced in the same reactions. There was no significant variability in fragment intensity in reactions that contained rPAI-1$_{23}$ and plasminogen or rPAI-1$_{23}$ and plasminogen and uPA. The amount of plasminogen at 80 kDa was substantially greater than the amount of the cleavage product. Very little of the plasminogen was converted to intact plasmin when relative intensities of all fragments were compared between immunoblots and zymograms. These results indicate that uPA plays a role in the reaction mixture by converting intact plasminogen into intact plasmin and converting cleaved plasminogen into a truncated plasmin of 34 kDa. rPAI-1$_{23}$-cleaved plasminogen was essential for the formation of the truncated plasmin and seemingly competed with uPA in a standard plasminogen reaction. The 34 kDa proteolytic protein that corresponds to rPAI-1$_{23}$-induced cleaved plasminogen product appears to be physiologically relevant as it is found in commercially available, purified plasmin and atherosclerotic plaques.

Accordingly, another aspect of the present invention is method of producing a 34 kDa truncated plasmin proteolytic protein. The truncated plasmin protein may be generated by combining plasminogen and rPAI-1$_{23}$ for a specified amount of time and subsequently adding uPA to the reaction. It is contemplated that one may recognize the production of a 34 kDa truncated plasmin proteolytic protein by its activity, size, and binding by an antibody specific for mini-plasmin. Preferably, the time required for rPAI-1$_{23}$ to enhance the conversion of plasminogen to plasmin is 15, 30, 45, 60 minutes or more, most preferably more than 45 minutes. The time required to convert plasmin to truncated plasmin via uPA will be dependent on the desired amount of truncated plasmin to be produced, however, times of 15, 30, 45, 60 minutes or more, preferably more than 45 minutes, are contemplated. The amount of reactants combined in accordance with this method of the invention will be dependent on the amount of product desired and may vary with the incubation time (e.g., longer incubation times may be necessary when lower concentrations of rPAI-1$_{23}$ are used to enhance the conversion of plasminogen to plasmin). It is contemplated that a 34 kDa truncated plasmin proteolytic protein produced by this method of the invention may be useful as an anti-angiogenic agent.

Reduced plasmin levels attributed to rPAI-1$_{23}$ indicated that there would possibly be a reduction in downstream activitation of plasmin by matrix metalloproteinases (MMPs) An RNase protection assay was performed by probing RNA isolated from endothelial cells treated with rPAI-1$_{23}$, rPAI-1$_{Hep23}$ or VEGF with a set of probes from various MMPs. It was found that at 18 hours of treatment, pro-angiogenic rPAI-1$_{Hep23}$ and anti-angiogenic rPAI-1$_{23}$ displayed significant differences in membrane type 1-matrix metalloproteinase (MT1-MMP) transcripts. The rPAI-1$_{23}$-treated cells had more than a 400% reduction in MT1-MMP transcript, as compared to rPAI-1$_{Hep23}$, and a 360% reduction when compared to VEGF-stimulated transcript. MT1-MMP has been shown to up-regulate VEGF expression (Sounni, et al. (2002) FASEB J. 16(6):555-64; Deriyugina, et al. (2002) Cancer Res. 62(2):580-8). Thus, results provided herein indicate that the rPAI-1$_{23}$ down-regulation of MT1-MMP and concurrent down-regulation of VEGF may, in part, account for a more profound anti-angiogenic activity of rPAI-1$_{23}$-Biochemical and in vitro analysis of angiostatin formation indicated that rPAI-1$_{23}$ and rPAI-1$_{A23}$ proteins selectively modulated angiostatin formation. Accordingly, in one embodiment of the present invention, rPAI-1 proteins lacking a reactive center loop and lacking at least a portion of a heparin-binding domain may be used in a method for modulating the formation of angiostatin which contains kringles 1-3 or kringles 1-4. In a preferred embodiment, a rPAI-1 protein for use in modulating angiostatin formation is rPAI-1$_{23}$ or rPAI-1$_{A23}$.

In vitro anti-angiogenic activity of the rPAI-1 proteins was analyzed. In an Annexin V binding assay, it was demonstrated that adherent bovine aortic endothelial cells (BAEC), 39% of the rPAI-1$_{23}$ and 19% of rPAI-1$_{A23}$-treated cells, were undergoing apoptosis. Whereas, only 4-7% of the rPAI-1$_{Hep23}$, rPAI-1$_{24}$, and yeast-treated cells were apoptotic, a value comparable to the endothelial control. This indicated that heparin-binding to rPAI-1$_{Hep23}$ protects the endothelial cells from apoptosis. Therefore, proteolytic cleavage products of rPAI-1$_{23}$ and rPAI-1$_{A23}$ may be involved with the induction of apoptosis. Thus, in another embodiment of the present invention, rPAI-1 proteins lacking a reactive center loop and lacking at least a portion of a heparin-binding domain may be used in a method for stimulating apoptosis. In a preferred embodiment, a rPAI-1 protein for use in stimulating apoptosis is rPAI-1$_{23}$ or rPAI-1$_{A23}$.

To further investigate the in vitro anti-angiogenic activity of the rPAI-1 proteins, cell proliferation in the presence of rPAI-1 proteins was examined. Bovine aortic endothelial cells were evaluated for their ability to proliferate after exposure to rPAI-1 proteins. The control cells proliferated at a rate of approximately one doubling in 48 hour. The rPAI-1$_{24}$-treated cells did not double in number during the first 48 hours, but doubled in the subsequent 48 hours. The rPAI-1$_{23}$- and rPAI-1$_{A23}$-treated cells did not increase in number in the 96 hour test period. In fact, the rPAI-1$_{23}$-treated cells decreased their number by 80% between 48 and 96 hours. There were 46% fewer apoptotic rPAI-1$_{A23}$-treated cells. Nearly 100% of the rPAI-1$_{23}$-and rPAI-1$_{A23}$-treated endothelial cells examined in a BrdU labeling assay incorporated BrdU into DNA; thus supporting low density in rPAI-1$_{23}$ and rPAI-1$_{A23}$-treated cells as a result of reduced number, and not loss of proliferation capability. The heparin sulfate-binding rPAI-1 protein supports full proliferation and cell survival while the poor or non-heparin sulfate-binding proteins impair cell number. Accordingly, in another embodiment of the present invention rPAI-1 proteins lacking a reactive center loop and lacking at least a portion of a heparin-binding domain may be used in a method for effectively reducing or inhibiting cell proliferation. In a preferred embodiment, a rPAI-1 protein for use in reducing or inhibiting cell proliferation is rPAI-1$_{23}$ or rPAI-1$_{A23}$.

Experiments focusing on tubule formation were also conducted to explore the in vitro anti-angiogenic activity of the rPAI-1 proteins. Chick aortic arch rings from 14-day chick embryos formed tubules in MATRIGEL™. The tubules proliferated and migrated extensively when stimulated with bovine brain extract (BBE). The rings that were exposed to rPAI-1$_{Hep23}$-BBE had a proliferation and migration rate at least equivalent to the control. In contrast, after 3 days of exposure to rPAI-1$_{23}$-BBE, new tubules extended from the aortic rings to approximately 50% of the length measured in the control or rPAI-1$_{Hep23}$-treated rings. By day 4, that difference was 65%. The newly formed tubules from the aortic rings treated with rPAI-1$_{A23}$ migrated about 50% less than the control on day 3. That difference remained nearly the same on day 4. There was a greater amount of proliferation near the periphery of the ring of rPAI-1$_{A23}$-treated samples when compared to the rPAI-1$_{23}$-treated rings. The branches of the rPAI-1$_{23}$-and rPAI-1$_{A23}$-treated rings were more flattened and tightly connected. Their branches appeared to fuse as they extended parallel. The differences observed in the newly formed tubules in the rPAI-1-treated samples are consistent with the data presented above, where it was shown that unlike rPAI-1$_{23}$ and rPAI-1$_{A23}$, the rPAI-1$_{Hep23}$ does not induce the formation of proteolytic fragments at a 34-38 kDa molecular mass corresponding to plasminogen kringles 1-3 and does not induce apoptosis in BAEC with a concomitant reduction in cell number.

The aortic ring studies indicated that rPAI-1$_{Hep23}$ did not block migration or proliferation of sprouting tubules in MATRIGEL™. Therefore, the ability of rPAI-1$_{Hep23}$ to stimulate tubule migration and proliferation in the absence of angiogenic growth factors, bFGF and VEGF was examined in an ex vivo assay. Aortic rings stimulated with a combination of VEGF and bFGF were used as a positive control. These experiments showed that rPAI-1$_{Hep23}$ was able to stimulate angiogenic tubules at a level comparable to that observed and measured in embryonic aortic rings stimulated with combined VEGF and bFGF.

An evaluation of rPAI-1$_{23}$ inhibition of VEGF in a breast tumor was performed ex vivo in excised murine breast adenocarcinoma tumors. The tumors were cut into equivalent, spoke-like pieces from the center of the excised tumor. The tumor pieces were placed in 6-well cell culture plates coated with MATRIGEL™. The tumor pieces were then coated with an additional thin layer of MATRIGEL™, incubated at 37° C. in human endothelial serum-free medium containing 10% FBS, VEGF (10 ng/mL) or VEGF (10 ng/mL) and rPAI-1$_{23}$ (0.6 nM). Tumors were cultured for 7 days during which time tubes formed in MATRIGEL™. Tumor cells metastasized and migrated to the extending vessels indicating that VEGF had caused the vessels to become permeable and hence releasing chemotactic factors. Conversely, rPAI-1$_{23}$/VEGF-treated tumors formed fewer numbers of tubes, appeared to be undergoing apoptosis, and were not proliferating. Thus, these data show in vivo inhibition of VEGF function in a tumor.

Inhibition of pancreatic tumor vessels and tumor growth in vivo using anti-angiogenic PAI-1 isoform rPAI-1$_{23}$ was also demonstrated. Using an animal model, it was shown that rPAI-1$_{23}$ effected a significant 61% reduction in tumor growth (rPAI-1$_{23}$, 30±7 vs. saline, 79±5 mm$^2$, p=0.01), thereby demonstrating that rPAI-1$_{23}$ is a potent suppressor of angiogenesis in cancers such as pancreatic ductal adenocarcinoma. Tumor volume measurements at the time of excision (rPAI-1$_{23}$, 64±22 vs. saline, 208±24 mm$^2$, p=0.01) corroborated the two dimensional measurements and also enabled the detection of a third saline-treated tumor that was undetected in the intact animal.

Figure 2A:
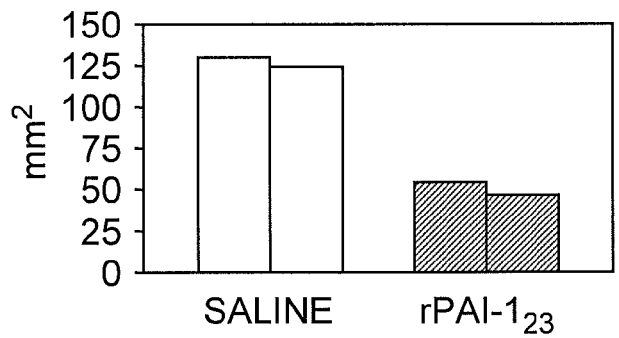
FIG. 2 shows pancreatic tumor area (FIG. 2A) and volume (FIG. 2B) of animals treated with saline or rPAI-1$_{23}$.
Figure 2B:
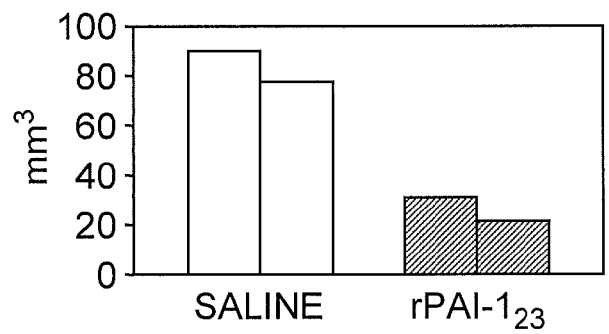

To measure and quantify the effect of rPAI-1$_{23}$ treatment, microCT volumes of the pancreatic tumors were obtained and manually segmented by drawing two dimensional regions of interest (ROIs) in consecutive coronal slices. The ROI contours were represented with cubic B-Spline curves and stacked in 3-D to provide volumetric representation of the tumors as closed triangulated meshes. The volume and area of the triangulated meshes encapsulating the tumors were determined and compared. The results of this analysis demonstrate that rPAI-1$_{23}$ treatment dramatically decreases tumor volume and area compared to control saline treatment (FIGS. 2A and 2B).

In vivo analysis of the proangiogenic properties of rPAI-1$_{Hep23}$ were also conducted. The cumulative results from three experiments indicated that proangiogenic rPAI-1$_{Hep23}$ protein stimulated 163% more neoangiogenic vessels than the MATRIGEL™ pellets containing VEGF/bFGF. The rPAI-1$_{23}$ protein, which has anti-angiogenic properties, reduced the number of neoangiogenic vessels to 1.3% of those formed in growth factor-stimulated pellets. The results indicate that rPAI-1$_{Hep23}$ has proangiogenic properties which are growth factor independent while rPAI-1$_{23}$ is anti-angiogenic.

The biochemical data provided herein demonstrated formation of a uPA·rPAI-1 complex that could possibly alter the activity of uPA or the rPAI-1 proteins. Therefore, the ability of endothelial cells to form tubes, migrate/extend, and proliferate in MATRIGEL™ following 24 hours of treatment with: each rPAI-1 protein; uPA and rPAI-1 added simultaneously, but independently; or a uPA·rPAI-1 complex were examined. Each rPAI-1 protein concentration was reduced so that uPA was in excess. It was determined that BAEC treated with rPAI-1$_{A23}$ formed a greater number of migrating tubules in MATRIGEL™ when compared to untreated or rPAI-1$_{23}$-treated BAEC. Further, connecting, migrating tubules and enhanced proliferation at focal centers were the obvious characteristics that resulted from scuPA and tcuPA treatment. The rPAI-1$_{A23}$-treated cells had fewer branch points and tubule extensions than scuPA- and tcuPA-treated cells. The rPAI-1$_{A23}$-treated endothelial cells that migrated in MATRIGEL™ formed tubules that appeared to be proliferating as they extend to result in greater tubule width; this effect was also seen in tcuPA-treated cells. Moreover, the effects of an rPAI-1$_{A23}$·tcuPA complex added to the BAEC increased proliferation at the focal centers, and increased tubule migration and extension. However, there was no apparent sprouting from the migrating tubules and the tubules appeared to be thinner. The overall effect was increased proliferation, migration and connecting of tubules, but a reduction in tubule width. Furthermore, when rPAI-1$_{A23}$ and tcuPA were added separately, but simultaneously, to the cultured cells, the tubule extension between focal centers was shortened. There was more proliferation along the migrating tubules, but the overall tubule density was reduced when compared with the tcuPA-treated cells. In addition, BAEC treated with a rPAI-1$_{A23}$·scuPA reaction mixture displayed enhanced migration of tubules that were connecting and branching, as well as increased proliferation. Those effects were reduced when rPAI-1$_{A23}$ and scuPA were added separately, but simultaneously to the cultured cells. However, rPAI-1$_{23}$ was able to maintain its inhibitory effect on tubule formation in MATRIGEL™. Following rPAI-1$_{23}$ treatment, single endothelial cells were embedded in the MATRIGEL™, but there was very little migration and proliferation of those cells. When uPA (single chain or two chain) and rPAI-1$_{23}$ were first reacted and then added to the BAEC, there was a small increase in tubule formation, extension and proliferation from the focal centers. The tubules that formed were spindly. When rPAI-1$_{23}$ and uPA were added separately but simultaneously, there was less proliferation and extension than observed in the cells that were treated with the reaction mixture. Overall, there was very little change in the anti-angiogenic effects of rPAI-1$_{23}$ when uPA was also added exogenously.

Migration of tubules appeared to be VEGF-dependent. By day 4, the rPAI-1$_{23}$-VEGF-treated rings displayed a reduction in the rate of migration similar to that measured in the BBE-treated samples. There was a significant difference in the structure of the VEGF-treated control tubules and the rPAI-1$_{23}$-VEGF-treated samples. VEGF-treated rings had a diffuse branching pattern with branches coming off at right angles, whereas the rPAI-1$_{23}$-VEGF-treated rings formed a very tightly packed mass of tubules that extended in parallel. These data show that rPAI-1$_{23}$ and rPAI-1$_{A23}$ are able to inhibit the migratory function of new sprouts from chick aortic rings stimulated with BBE. The rPAI-1$_{23}$ protein inhibits the migration of new sprouts stimulated with VEGF. In the rPAI-1$_{23}$ and rPAI-1$_{A23}$-treated aortic rings apoptosis of sprouting endothelial cells was observed. The apoptosis appeared to result in breakage of the tubule. Hence, in a further embodiment of the present invention, rPAI-1 proteins lacking a reactive center loop and lacking at least a portion of a heparin-binding domain may be used in a method for inhibiting cell migration. In a preferred embodiment, a rPAI-1 protein for use in inhibiting cell migration is rPAI-1$_{23}$ or rPAI-1$_{A23}$.

The modulation of VEGF from a complex with heparin by rPAI-1 proteins was analyzed. Variable concentrations of each rPAI-1 protein were incubated with a VEGF-heparin complex to examine the release and/or activation of VEGF-A.

VEGF activation and release from the complexes were then tested in the presence of activator molecules uPA or plasmin. Western blot analysis of the complexes was conducted with an antibody against heparin-binding VEGF-A isoforms.

Experiments were conducted with the VEGF-A$_{165, 189, 206}$ isoform in an rPAI-1-VEGF-heparin complex containing activator molecules uPA or plasmin. When rPAI-1$_{23}$ was part of the complex, there were only traces of the 46 kDa activated VEGF-A$_{165, 189, 206}$. In the presence of rPAI-1$_{A23}$, VEGF was released from heparin in the absence or presence of either uPA or plasmin. Similarly, the presence of rPAI-1$_{24}$ in the mixture with VEGF-heparin resulted in the release of active VEGF at all concentrations of rPAI-1$_{24}$. In the rPAI-1$_{24}$-containing reactions, the VEGF release occurred in the presence of uPA or plasmin. Reaction mixtures containing rPAI-1$_{Hep23}$ showed activated VEGF in reactions containing low concentrations of rPAI-1$_{Hep23}$ in the absence or presence of either uPA or plasmin. At higher concentrations of rPAI-1$_{Hep23}$, there was a blockage of VEGF release and an increase in VEGF-containing fragments between 60 and 80 kDa. The high molecular mass fragments containing VEGF had cross-reactivity with VEGF-B$_{186}$ and were indicative of the 60-62 kDa active VEGF-B$_{186}$ homodimer (Cao, et al. (1999) supra). The greater than 80 kDa molecular mass containing VEGF also existed in samples containing rPAI-1$_{23}$, rPAI-1$_{A23}$, and rPAI-1$_{24}$. However, the samples containing rPAI-1$_{Hep23}$ clearly had a greater amount of VEGF-A complexed at a high molecular mass. These experiments showed that rPAI-1$_{A23}$ and rPAI-1$_{24}$ do not block the activation or release of VEGF from a complex with heparin. Although rPAI-1$_{A23}$ and rPAI-1$_{24}$ both have a partial heparin-binding domain, only rPAI-1$_{24}$ has RCL. The RCL may alter the conformation such that the partial heparin domain in rPAI-1$_{24}$ is obscured and unable to block the release of activated VEGF. On the other hand, both rPAI-1$_{23}$ and rPAI-1$_{Hep23}$ are able to block the release of VEGF from a complex with heparin. These data indicate that the heparin-binding domain in each of these two isoforms participates in blocking the release of active VEGF-A and that partial heparin-binding is more effective in blocking VEGF-A activation and/or release. These findings indicate that the ability of rPAI-1$_{23}$ to block growth and vessel sprouting may be due to its ability to block VEGF activation.

Experiments were also conducted to determine which VEGF isoforms were complexed with heparin-rPAI-1$_{23}$ at the high molecular mass as seen in the previous experiments. For these experiments, DTT was added to the final reaction mixture containing VEGF-heparin-rPAI-1$_{23}$+uPA (or plasmin) for 2.5 hour at 37° C. The rPAI-1$_{23}$-VEGF-heparin complexes contained multiple-sized VEGF fragments representative of mature or active VEGF-A$_{165, 189}$: the fragment less than 34 kDa observed in this experiment corresponded to activated VEGF-A$_{189}$ (Plouet, et al. (1997) supra; Keyt, et al. (1996) *J. Biol. Chem.* 271:7788-7795); the 34-38 kDa fragments corresponded to plasmin or uPA activated VEGF-A$_{165,189}$ Plouet, et al. (1997) supra; Keyt, et al. (1996) *J. Biol. Chem.* 271:7788-7795); the 40-45 kDa fragments corresponded to uPA-matured VEGF-A$_{189}$ or VEGF-A$_{165}$ (Plouet, et al. (1997) supra; Keyt, et al. (1996) *J. Biol. Chem.* 271:7788-7795); and the 50-52 kDa band was the molecular mass of mature, but not active VEGF (Plouet, et al. (1997) supra).

In VEGF-heparin complexes containing lower concentrations of rPAI-1$_{23}$ protein, there were activated VEGF fragments between 30 and 42 kDa which corresponded to the reported sizes for processed VEGF-A$_{165, 189, 206}$. The fragments that migrated at 36-38 kDa were also in reactions containing uPA or plasmin. The most predominant VEGF fragment released from a VEGF-heparin-rPAI-1$_{23}$ complex was seen near 50 kDa (mature VEGF) in the absence of uPA and plasmin. When the rPAI-1$_{23}$ protein concentration was increased to 30 nM, the active VEGF at 50 kDa was absent and the products were approximately 30, 38-42 kDa which corresponded in size to uPA-matured VEGF-A$_{189}$ and VEGF-A$_{165}$, or plasmin-activated VEGF-A$_{189}$. In mixtures containing a VEGF-heparin-rPAI-1$_{Hep23}$ complex, the associated VEGF remained at a higher molecular mass (greater than 80 kDa), except when rPAI-1$_{Hep23}$ was at a low concentration. The rPAI-1$_{Hep23}$ protein conformation maintained VEGF-A$_{165, 189, 206}$ in a complex with heparin. Therefore, the rPAI-1$_{23}$ may be used to block the release of multiple forms of matured, activated, and processed (uPA and plasmin cleaved) VEGF-A fragments reported for heparin-binding VEGF-A$_{165, 189}$ isoforms.

Analysis of VEGF-A contained within the culture medium of rPAI-1-treated endothelial cells was also conducted. The rPAI-1$_{23}$-treated cells primarily contain VEGF-A fragments at a molecular mass greater than 50 kDa. A small fraction of VEGF fragments at a molecular mass less than 50 kDa were also observed in the rPAI-1$_{23}$-treated samples. The fragments greater than 50 kDa were representative of mature or pro-VEGF and those less than 50 kDa corresponded to active VEGF. In the culture medium samples collected rPAI-1$_{A23}$-treated cells there was an abundance of VEGF-A fragments at a molecular mass of 36-45 kDa at all time points (6, 15, 24, 30, 48, and 72 hours). This molecular mass corresponded to active or uPA/plasmin processed, active VEGF-A. All rPAI-1$_{A23}$-treated samples also contained mature or pro-VEGF at a molecular mass greater than 50 kDa. One of the inactive fragments in the 15 hour time point sample was absent in samples at 6, 24, 30, 48, and 72 hours. The culture media from all untreated and rPAI-1$_{24}$-treated cells, contained active VEGF and a small amount of processed, activate VEGF. The culture medium samples from the rPAI-1$_{Hep23}$-treated cells primarily contained inactive VEGF and lesser amounts of processed, active VEGF. The results of these experiments clearly showed that VEGF in rPAI-1$_{A23}$-treated culture medium contains a much greater amount of active VEGF, mostly representative of uPA or plasmin processed VEGF. Similar VEGF fragments were absent or present to a lesser degree in the untreated or rPAI-1$_{23}$-, rPAI-1$_{Hep23}$-, and rPAI-1$_{24}$-treated cells. The culture media from rPAI-1$_{24}$-treated and untreated cells contained a greater amount of active, unprocessed VEGF than the media from rPAI-1$_{23}$-, rPAI-1$_{A23}$-, or rPAI-1$_{Hep23}$-treated cells. These data corresponded with the biochemical analysis of VEGF released from a complex with heparin and rPAI-1 proteins. The molecular mass of all of the VEGF fragments corresponded to dimeric VEGF-A despite the rigorous reducing conditions applied to all samples.

Differences in heparan sulfate-bound VEGF-A isoforms in rPAI-1-treated cells were analyzed using two different antibodies. Immunoblots were probed for VEGF-A with an antibody specific for epitopes common to VEGF-A$_{165, 189, 205}$. The results of these experiments showed that, at the 12-hour time point, the rPAI-1$_{Hep23}$-and rPAI-1$_{24}$-treated cells contained two fragments of VEGF-A at a molecular mass near 58 kDa. In the rPAI-1$_{23}$-treated, rPAI-1$_{A23}$-treated, and untreated samples, VEGF-A was absent or barely visible. However, when two competing antibodies specific for VEGF-A were simultaneously incubated with immunoblots containing proteins released from a heparinase digest, the rPAI-1$_{23}$-treated, rPAI-1$_{A23}$-treated, and untreated cells show VEGF-A released from heparan sulfate. Among the samples, the rPAI-1$_{23}$-treated cells at the six-hour time point had the greatest amount of detectable VEGF-A released in the enzymatic digest. The VEGF was seen as two distinct fragments with a small difference in molecular mass. Each fragment corresponded to the molecular mass of dimeric VEGF, despite the rigorous reducing conditions. By 12 hours, VEGF was not detected in rPAI-1$_{23}$-treated cells. However, at the 12-hour time point, the rPAI-1$_{A23}$-treated and the untreated cells showed a variable molecular mass in VEGF released as a result of the digest. The VEGF fragments in the rPAI-1$_{23}$-treated samples were very close to 50 kDa, whereas, the VEGF fragments in the untreated and the rPAI-1$_{A23}$-treated cells corresponded to a molecular mass that was more representative of VEGF-A$_{189}$ or VEGF-A$_{206}$. The rPAI-1$_{Hep23}$-and rPAI-1$_{24}$-treated cells did not show the release of heparan sulfate-bound VEGF when the blot was probed with competing antibodies. The results of these sets of experiments showed that different VEGF-A isoforms were released with the heparinase digest, depending upon the rPAI-1 treatment. The use of competing antibodies exposed binding sites in rPAI-1$_{23}$-treated, rPAI-1$_{A23}$-treated, and untreated cells that were not detected with the single antibody probe for VEGF-A$_{165, 189, 205}$. The most pronounced difference was the intensity and molecular mass of VEGF-A at the six-hour time point in rPAI-1$_{23}$-treated cells. It corresponded to a molecular mass near that reported for dimeric mature/pro-VEGF-A$_{165}$ and/or mature VEGF-A$_{189}$. Because the VEGF fragments became intensely visible upon competition with an antibody specific for the active site of VEGF-A$_{165}$, the data indicated that the fragments slightly above 50 kDa were VEGF-A$_{165}$. These data also showed that the conformation of VEGF was altered as a result of rPAI-1$_{23}$ treatment. Also, the presence of extracellular matrix-associated VEGF-A at the 6-hour time point was coordinate with the absence of activated VEGF in the culture medium of rPAI-1$_{23}$-treated cells at 6 hours. The VEGF-A fragments that become visible at the 12 hour time points in untreated or rPAI-1$_{A23}$-treated cells were at a greater molecular mass corresponding to pro-VEGF-A$_{189}$ or pro-VEGF-A$_{206}$, the isoforms that had the greatest affinity for heparan sulfate. Similarly, the VEGF detected in all samples was representative of dimeric VEGF, despite the reducing conditions.

Additional studies were conducted to more clearly define the mechanism by which rPAI-1$_{23}$ prevents the release of VEGF from heparan sulfate. Taking into consideration that rPAI-1$_{23}$, uPA and VEGF have binding domains for heparin/heparan sulfate; rPAI-1$_{23}$ binds uPA at the additional uPA binding domain; and uPA can bind to and activate pro-VEGF; it was determined whether rPAI-1$_{23}$ was retaining VEGF in a complex with uPA. Primarily, it was determined whether treatment with rPAI-1$_{23}$ could alter the binding affinity of VEGF for a specific heparan sulfate chain. Moreover, it was determined whether an rPAI-1$_{23}$ or uPA-rPAI-1$_{23}$ complex prevented the release of VEGF from a specific heparan sulfate chain. Thus, BAEC were treated either with anti-angiogenic rPAI-1$_{23}$ protein, rPAI-1$_{23}$ complexed with uPA, or various pro-angiogenic molecules (VEGF, uPA, bFGF, rPAI-1$_{Hep23}$) for 16 hours at 37° C. The treatment molecules were removed using Hanks' balanced salt solution (HBSS) washes and subsequently 1 Unit/mL of either heparinase I or heparinase III was added to the treated cells for 1 hour. Proteins released by heparinase treatment were collected and equivalent amounts of protein were separated in a 4-20% SDS reducing polyacrylamide gel. Immunoblots containing the separated proteins were probed with two competing VEGF-specific antibodies. In cells treated with rPAI-1$_{23}$, activated VEGF (monomer at 16 kDa) was not released from heparan sulfate during heparinase I treatment, rather inactive and/or complexed VEGF was observed near 50 and 80 kDa. Similarly, VEGF was not released from heparan sulfate when cells were treated with rPAI-1$_{23}$/uPA complex. However, if uPA and rPAI-1$_{23}$ were added separately, but simultaneously, to the culture medium of endothelial cells, VEGF was released from heparan sulfate by heparinase I treatment. Heparinase III treatment also did not liberate VEGF from cells treated with an rPAI-1$_{23}$/uPA complex, however, VEGF was released from cells treated with rPAI-1$_{23}$. Thus, there is more VEGF associated with heparan sulfate containing side chains which may be liberated by heparinase I digestion as compared to heparinase III digestion. In addition, cells treated with pro-angiogenic rPAI-1$_{Hep23}$ have a much greater amount of released active VEGF at a molecular mass between 34 and 50 kDa than any of the other pro-angiogenic molecules (uPA, VEGF, or bFGF). However, treating cells with a rPAI-1$_{Hep23}$/uPA complex blocks the release active VEGF from heparan sulfate. Accordingly, these data indicate that an rPAI-1$_{23}$/uPA complex is involved in the inhibition of VEGF release from heparan sulfate and uPA can inhibit the release of VEGF when complexed with rPAI-1$_{Hep23}$.

Subsequent analysis was conducted to examine VEGF binding to sites on heparan sulfate and to VEGF receptors. Endothelial cells were first treated with 0.6 nM rPAI-1$_{23}$ or 10 ng/mL VEGF for 2, 4 and 16 hours. Subsequently, the cells were placed on ice and washed with ice-cold phosphate buffered saline (PBS) before the addition of $^{125}$I-VEGF. After a one-hour incubation with $^{125}$I-VEGF on ice, cells were washed extensively with ice-cold PBS containing 0.05% bovine serum albumin. The cells were then washed with 0.35 M NaCl for 10 minutes to remove VEGF bound to heparan sulfate. The cells were also washed with ice-cold PBS containing 0.05% BSA before the addition of 1 N NaOH for 30 minutes. Fractions containing released VEGF or dissolved membrane proteins (i.e., dissolved in 1 N NaOH) were collected and prepared for counting the iodinated VEGF. Further, triplicate samples of each test and time point were prepared to perform a cell count. The cell count was used to normalize the DPM with cell number.

The results of these experiments showed that following 16 hours of treatment, the number of available VEGF binding sites on heparan sulfate in rPAI-1$_{23}$-treated endothelial cells were more than three times that of the untreated endothelial cell control. In contrast, the number of receptor binding sites on rPAI-1$_{23}$-treated cells was very similar to that of the untreated cells, indicated that VEGF was bound to available receptors. Competition assays with cold VEGF verified that the labeling was VEGF-specific.

In vitro experiments were conducted with Annexin V to measure apoptosis in bovine and porcine aortic endothelial cells treated with rPAI-1$_{23}$ protein. These data showed that rPAI-1$_{23}$ treatment resulted in 300% more apoptotic bovine aortic endothelial cells (BAEC) as compared to porcine aortic endothelial cells (PAEC). Since PAEC do not express VEGFR-1 or VEGFR-2, these experiments clearly showed that most, but not all, of the apoptosis induced by rPAI-1$_{23}$ was through a mechanism that blocked/inhibited VEGF receptors 1 and/or 2. 60% of the apoptosis in rPAI-1$_{23}$-treated BAEC could be attributed to inhibition of VEGF-VEGFR functional activity. These data demonstrate a mechanism whereby rPAI-1$_{23}$ blocked release of active VEGF-A thereby preventing (or limiting) binding to VEGF receptors to result in apoptosis. The 65% reduction in migration of VEGF-stimulated tubules from rPAI-1$_{23}$-treated embryonic chick aortic rings provides a mechanism which inhibits VEGFR-2 function. Accordingly, in a further embodiment of the present invention, rPAI-1 proteins used to block the release of VEGF from a VEGF-heparin complex lack an RCL domain and lack all or at least a heparin-binding domain as found in, for example, rPAI-1$_{23}$, rPAI-1$_{24}$ and rPAI-1$_{Hep23}$. In a preferred embodiment, rPAI-1$_{23}$ is used to block the release of VEGF from a VEGF-heparin complex.

Further, in vitro experiments were conducted to evaluate the effect of rPAI-1$_{23}$ on MT1-MMP-mediated cellular phenotypes. The up-regulated expression of VEGF by MT1-MMP is associated with an invasive phenotype, particularly on a type I collagen matrix (Murakami, et al. (1999) *Neoplasia* 1(5):424-30; Seiki (2003) *Cancer Lett.* 194(1):1-11). Thus, the activity of rPAI-1$_{23}$ was evaluated using endothelial cells plated onto a type I collagen matrix. Endothelial cells were seeded onto 6-well culture plates and allowed to adhere for 1 hour before the addition of a type I collagen coat over the cells. The plates were incubated at 37° C. for 1 hour to allow the collagen to congeal. Dulbecco's Modified Eagle's Medium containing VEGF (10 ng/mL), rPAI-1$_{23}$ (0.6 nM) or rPAI-1$_{Hep23}$ (0.6 nM) was added to each well and cultures were incubated at 37° C. for seven days; medium containing the anti- or pro-angiogenic molecules was replaced every 48 hours.

Most BAECs treated with rPAI-1$_{23}$ were apoptotic within the first 24 hours and looked the same throughout the seven day incubation. Conversely, rPAI-1$_{Hep23}$-and VEGF-stimulated BAECs formed tubes on the collagen matrix and the untreated cells formed incomplete tubes. These data are consistent with the RNase protection assays which showed that anti-angiogenic rPAI-1$_{23}$ down-regulated MT1-MMP and pro-angiogenic rPAI-1$_{Hep23}$ and VEGF up-regulated MT1-MMP. The extensive apoptosis induced by rPAI-1$_{23}$ by 24 hours indicates a possible mechanism by which rPAI-1$_{23}$ reduces the invasiveness of tumors.

The in vivo physiological relevance of the various cleaved isoforms of PAI-1 was examined in patient samples isolated from two cardiovascular clinical studies. In one cardiology study, patients were evaluated for diseased vessels and the number of collaterals. Blood was drawn from said patients and plasma was examined for cleaved PAI-1. Thirty-five patient samples were examined. Of these patients, some had cleaved PAI-1 in the plasma at a molecular mass near 28 kDa and some had no observable cleaved PAI-1. All samples examined had intact PAI-1 of variable intensities. In some samples there was also evidence of a cleavage product at a molecular mass close to intact PAI-1. This fragment size has been reported in vitro studies and is correlated with thrombin. Plasminogen kringle domains 1-3 were also examined in these patient samples. A correlation between the presence of cleaved PAI-1 near 28 kDa and plasminogen kringles 1-3 at 34 kDa was observed.

Atherosclerosis is a chronic disease of large and medium size arteries and is a significant underlying cause of coronary, peripheral and carotid artery disease. Neoangiogenesis associated with more advanced stages of human atherosclerosis is found in the vasa vasorum, the microvasculature in the adventitial layer of large arteries in humans. Vasa vasorum have also been correlated with atherosclerotic lesion size in hypercholesterolemic animal models (Langheinrich, et al. (2006) *Arterioscler. Thromb. Vasc. Biol.* 26:347-352; Moulton, et al. (2003) *Proc. Natl. Acad. Sci. USA* 100:4736-4741; Wiliams, et al. (1988) *Cir. Res.* 62:515-523). It is thought that the vasa vasorum serves as a means of supplying nutrients to the vessel wall. In atherosclerosis, vasa vasorum are considered to be the conduit for nutrient supplies to the plaque. Inhibition of neovascularization in the vaso vasorum is associated with reduced plaque progression (Moulton, et al. (2003) supra). However, the role of angiogenesis in atherosclerotic plaque growth is unclear.

Accordingly, in a second clinical study, atherosclerotic plaques were surgically-removed and the presence of PAI-1 proteins was examined. Proteins were isolated from the plaques by tissue homogenization on ice in the presence of protease inhibitors or from proteins released from plaque cultures. Subsequently, the proteins were analyzed for cleaved PAI-1 and plasminogen cleavage products. Cleaved PAI-1 near 28 kDa was present in all examined plaques at variable amounts. Further, there was an enormous difference in plasminogen cleavage products detected with kringle 1-3 antibody probe. In some samples, fragments near 50 kDa were observed. In other samples, doublets between 28 and 34 kDa were observed. Moreover, cleaved plasminogen was absent or barely detectable in some samples.

It was further determined whether rPAI-$1_{23}$ exhibited anti-angiogenic activity in an animal model of atherosclerosis. To study the effects of rPAI-$1_{23}$ on plaque growth, Sudan IV-stained plaque areas were measured and their size relative to the total area of the descending artery was calculated. Measurements were taken in mice that were fed high fat, high cholesterol for 14 weeks before receiving 6 weeks of rPAI-$1_{23}$ or saline treatment while maintaining the diet. Control animals received normal chow diet and received 6 weeks of saline treatment. Plaque area in the rPAI-$1_{23}$ treatment group was reduced by 60% (p<0.001) when compared to the saline-treated group fed the same diet. Unexpectedly, the amount of lipid measured in rPAI-$1_{23}$-treated mice was comparable to those fed a normal diet and received saline treatment for six weeks. The Sudan IV-stained area in the aortic arch of the rPAI-$1_{23}$-treated group and normal chow saline group was 30% (p<0.001) less than the high fat, high cholesterol saline-treated mice. The data indicate that mice receiving rPAI-$1_{23}$ treatment experienced a significant reduction in plaque area in the descending aorta and the aortic arch.

Average total cholesterol measurements were not significantly different between the rPAI-$1_{23}$-and saline-treated mice fed a high fat, high cholesterol diet (rPAI-$1_{23}$, 801±39 vs. saline, 938±47 mg/dl). Mice fed chow diet and received saline treatment had a cholesterol value of 267±7 mg/dl. All groups were in a normal range for their specific diet.

To examine vessel density in relationship to plaque area in the descending aorta, vessels located in plaque areas were probed for endothelial marker CD-31 and confocal Z-stack microscopic images were acquired. The vessels in the plaque area of the rPAI-$1_{23}$ treatment group were significantly fewer in number than the saline treatment group that was also fed the high fat, high cholesterol diet. The plaques were then stained for Sudan IV and en face whole mount confocal images showed that the plaque lipid area in the rPAI-$1_{23}$ treatment group was distinctly smaller and the Sudan IV stain was of lesser intensity than either of the two saline treatment groups. The collective data indicated that the rPAI-$1_{23}$ treatment group reduced vessel density and lipid content in the plaque area.

Figure 3:
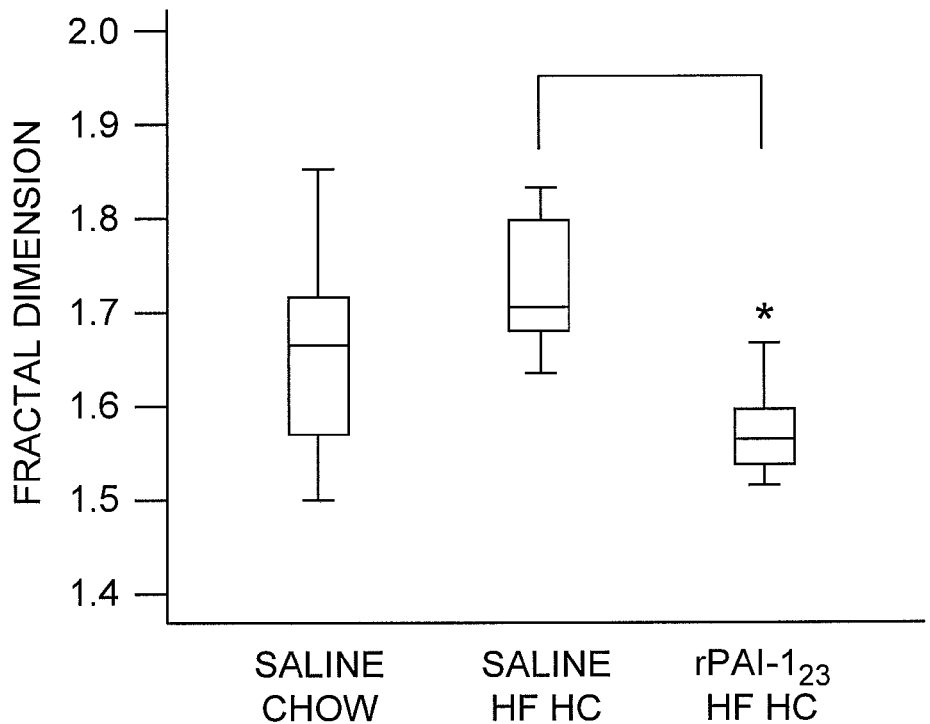
FIG. 3 shows MatLab calculations of vessel area and length. Reconstructed Z-stack images transformed to black and white images with VELOCITY software were used for fractal analysis using a MatLAB script that calculates vessel vs. non-vessel segments. Treatments included mice fed chow diet and received saline treatment (saline chow, n=4); mice fed Paigen's high fat, high cholesterol, no cholate diet and saline treatment (saline HF HC, n=7); mice fed Paigen's high fat, high cholesterol, no cholate diet and rPAI-1$_{23}$ treatment (rPAI-1$_{23}$ HF HC, n=8) . Note the reduced vessel fractal dimension in the rPAI-1$_{23}$ treatment group. Data shown as mean±standard error of the mean (SEM) and p values were determined by ANOVA. *p<0.05 vs. control.

To confirm the differences observed in confocal images, computer-assisted reconstruction of the vessels was performed using VELOCITY software. The density of reconstructed vessels in rPAI-$1_{23}$-treated mice was significantly reduced when compared to the saline, high fat, high cholesterol group. Skeletonized reconstructed vessel images indicated that vessels in rPAI-$1_{23}$-treated and saline-treated, normal chow fed mice were in discontinuous fragments lacking complete vascular enclosures, while the saline-treated, high fat, high cholesterol group had numerous complete vascular structures. The calculated fractal dimension (FIG. 3) was significantly smaller in the rPAI-$1_{23}$-treated, high fat, high cholesterol mice compared to the saline group on the same diet, indicating a change in the vascular branching pattern.

Furthermore, a 37% (p=0.01) reduction in total vessel area and a 43% (p=0.004) reduction in vessel length in rPAI-$1_{23}$-treated mice maintained on high fat, high cholesterol compared to the saline counterpart was observed. There was no significant difference in the control chow diet, saline-treated mice compared to either rPAI-$1_{23}$ or saline treatment in high fat, high cholesterol diet groups. From this series of experiments it was concluded that rPAI-$1_{23}$ inhibits vessel density in the plaque area and that the vessels regressed.

To determine the extent of plaque growth at a site more proximal to the origin of the diseased vessels, histologic cross sections of the left carotid artery were analyzed for morphological changes. Measurements of the vessel wall circumferences in hematoxylin and eosin-stained sections of the left carotid artery determined that there were no significant differences between the rPAI-$1_{23}$-and saline-treated mice that were fed a high fat, high cholesterol diet (rPAI-$1_{23}$, 30.5±1.2 and saline, 33.7±2.45 mm). The circumferences in both groups were significantly greater than the chow diet, control group (23.7±0.8 mm, p<0.001), which indicated that the vessel wall in rPAI-$1_{23}$-and saline-treated, high fat, high cholesterol groups had undergone outward remodeling. However, measurements of the luminal area in the two groups on high fat, high cholesterol diet showed that the rPAI-$1_{23}$-treated group had a 1.8-fold greater luminal area than the saline-treated group (rPAI-$1_{23}$, 46±4 vs. saline, 26±4 mm$^2$, p=0.03). Conversely, the plaque area in the rPAI-$1_{23}$ treatment group was reduced by 68% when compared to its saline counterpart (rPAI-$1_{23}$, 23±2 vs. saline, 71±6 mm$^2$, p<0.001). It was concluded from this set of experiments that the left carotid artery in both test groups fed high fat, high cholesterol underwent outward remodeling prior to the initiation of rPAI-$1_{23}$ or saline treatment. The effects of rPAI-$1_{23}$ significantly reduced the plaque area and increased the luminal area during the six weeks of treatment. These data demonstrate that rPAI-$1_{23}$ inhibits angiogenic vasa vasorum, reduces plaque growth, and promotes plaque regression. Therefore, rPAI-$1_{23}$ is useful in the treatment of atherosclerosis.

PAI-1 can be cleaved at the P1 and P'1 residues of the RCL, resulting in a substrate with a molecular mass of 39 kDa (Dhanabal, et al. (1999) *J. Biol. Chem.* 274:11721-11726; Aleshkov, et al. (1996) *J. Biol. Chem.* 271:21231-21238; Declerck, et al. (1992) *J. Biol. Chem.* 267:11693-11696). The amount of substrate PAI-1 (RCL cleaved, inactive) is increased during the interaction with PAI-1 with thrombin in the presence of heparin and vitronectin (Van Meijer, et al. (1997) *Blood* 90:1874-1882). A smaller, cleaved PAI-1 fragment (<31 kDa) has been shown to be produced as a result of addition of heparin and thrombin to a pre-existing PAI-1 thrombin complex (Patston and Schapira (1994) *Blood* 84:1164-1172). The deletions at the carboxy-terminus exclude the RCL in three of the four rPAI-1 isoforms described herein and each of these proteins function differently with respect to pro- and anti-angiogenic mechanisms. Therefore, the functional activity of these proteins is not solely dependent upon the absence of the reactive center loop. The structural difference in rPAI-$1_{23}$, rPAI-$1_{A23}$, and rPAI-$1_{Hep23}$ is the heparin (heparan sulfate)-binding domain which accounts for the differences in functional activity of the three proteins. The novel functional activity of these isoforms of PAI-1 makes them useful in differentially modulating angiogenesis. In a particular embodiment of the present invention, an rPAI-1 isoform lacking an RCL domain and lacking a least a portion of the heparin-binding domain is useful in a method of blocking, reducing or decreasing angiogenesis. Exemplary isoforms lacking an RCL domain and at least a portion of the heparin-binding domain include, but are not limited to, rPAI-$1_{23}$ and rPAI-$1_{A23}$. In another preferred embodiment of the present invention, an rPAI-1 isoform lacking an RCL domain and containing a complete heparin-binding domain is useful in a method of stimulating or increasing angiogenesis. An exemplary isoform lacking an RCL domain and containing a complete heparin-binding domain includes, but is not limited to, rPAI-$1_{Hep23}$.

The rPAI-$1_{23}$, rPAI-$1_{Hep23}$ and rPAI-$1_{A23}$ isoforms of the present invention are useful in treating diseases or processes that are mediated by, or involve, angiogenesis. The present invention provides a method of treating an angiogenesis-mediated disease with an effective amount of a PAI-1 isoform lacking the RCL domain and either containing a complete heparin-binding domain or lacking at least a portion of the heparin-binding domain. It is contemplated that rPAI-1 isoforms lacking the RCL domain and lacking at least a portion of the heparin-binding domain, e.g., rPAI-$1_{A23}$ and rPAI-$1_{23}$, would be useful as anti-angiogenic agents. Angiogenesis-mediated diseases for which anti-angiogenic agents would be useful in alleviating the signs or symptoms of include, but are not limited to, solid tumors; blood bourne tumors such as leukemias; tumor metastasis; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. Anti-angiogenic agents are also useful in the treatment of diseases that have angiogenesis as a pathologic consequence such as cat scratch disease (Rochele minalia quintosa) and ulcers (Helicobacter pylori). Furthermore, PAI-1 isoforms lacking the RCL domain and lacking at least a portion of the heparin-binding domain are effective in the treatment of diseases of excessive or abnormal stimulation of endothelial cells. These diseases include, but are not limited to, intestinal adhesions, atherosclerosis, scleroderma, and hypertrophic scars, i.e., keloids.

Anti-angiogenic agents of this invention are also useful for promoting plaque regression. In this regard, the administration of an effective amount of a PAI-1 isoform lacking the RCL domain and lacking at least a portion of the heparin-binding domain achieves at least a 40%, 50%, 60%, 70%, 80%, or more decrease in the area of the plaque as compared to a plaque which has not been contacted with the PAI-1 isoform.

Further contemplated is rPAI-1 isoforms lacking the RCL domain and containing a complete heparin-binding domain, e.g., rPAI-$1_{Hep23}$ as proangiogenic agents. Proangiogenic agents would be useful for stimulating wound healing, replacing clogged arteries to improve circulation in patients with arterial clogging, and treating various types of heart disease to promote the growth of blood vessels thereby reducing the need for bypass surgery.

While specific PAI-1 isoforms are disclosed herein, it would be well within the ability of the skilled artisan, using the results provided by this disclosure, to generate additional PAI-1 isoforms lacking at least a portion of the heparin-binding domain. For example, one could remove residue Lys-65 and/or Lys-69 of the rPAI-$1_{Hep23}$ isoform to decrease the proangiogenic activity of this isoform.

In general, those skilled in the art will appreciate that minor deletions or substitutions may be made to the amino acid sequences of rPAI-1 isoforms of the present invention without unduly adversely affecting the activity thereof. Thus, isoforms containing such deletions or substitutions are also contemplated. In isoforms containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/hydrophilicity, size and configuration, so that amino acids are substituted with other amino acids having essentially the same functional properties. For example: Ala may be replaced with Val or Ser; Val may be replaced with Ala, Leu, Met, or Ile, preferably Ala or Leu; Leu may be replaced with Ala, Val or Ile, preferably Val or Ile; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; KGln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on function.

The rPAI-1 isoforms of the present invention can be purified from host cells which express the same, in accordance with known techniques, or even manufactured synthetically. Alternatively, the rPAI-1 isoforms may be used as part of a gene therapy approach.

Recombinant PAI-1 proteins may be produced using methods exemplified herein for using other well-known methods for long-term, high-yield production of recombinant proteins. For example, nucleic acid sequences encoding, e.g., human, porcine, or bovine PAI-1, may be recombinantly engineered, using well-known methods, to produce the rPAI-1 isoforms of the present invention which lack the RCL domain and contain a complete heparin-binding domain or lack at least a portion of a heparin-binding domain as defined herein. A recombinant nucleic acid sequence encoding a rPAI-1 isoform may then be incorporated into an expression vector. An expression vector is a replicable DNA construct in which a nucleic acid sequence encoding an rPAI-1 isoform of the present invention is operably linked to suitable control sequences capable of effecting the expression of the isoform in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation.

Vectors comprise plasmids, viruses (e.g., adenovirus, cytomegalovirus), phage, retroviruses and integratable DNA fragments (i.e., fragments integratable into the host genome by recombination). The vector replicates and functions independently of the host genome, or may, in some instances, integrate into the genome itself. Expression vectors should contain a promoter and RNA binding sites that are operably linked to the gene to be expressed and are operable in the host organism.

Suitable host cells include prokaryotes, yeast cells, or higher eukaryotic organism cells. Prokaryote host cells include gram negative or gram positive organisms, for example *Escherichia coli* (*E. coli*) or *Bacilli*. Higher eukaryotic cells include established cell lines of mammalian origin. Exemplary host cells are *E. coli* W3110 (ATCC 27,325), *E. coli* B, *E. coli* X1776 (ATCC 31,537), *E. coli* 294 (ATCC 31,446). A broad variety of suitable prokaryotic and microbial vectors are available. *E. coli* is typically transformed using pBR322. See Bolivar, et al., ((1977) Gene 2:95). Promoters most commonly used in recombinant microbial expression vectors include the beta-lactamase (penicillinase) and lactose promoter systems (Chang, et al. (1978) *Nature* 275:615; Goeddel, et al. (1979) *Nature* 281:544), a tryptophan (trp) promoter system (Goeddel, et al. (1980) *Nucl. Acids Res.* 8:4057; EP36,776) and the tac promoter (De Boer, et al. (1983) *Proc. Natl. Acad. Sci. USA* 80:21). The promoter and Shine-Dalgarno sequence (for prokaryotic host expression) are operably linked to the DNA of the present invention, i.e., they are positioned so as to promote transcription of the messenger RNA from the DNA.

Eukaryotic microbes such as yeast cultures may be transformed with suitable expression vectors as exemplified herein. Alternatively, *Saccharomyces cerevisiae* may be used. Yeast vectors may contain an origin of replication from the 2 micron yeast plasmid or an autonomously replicating sequence (ARS), a promoter, DNA encoding the desired protein, sequences for polyadenylation and transcription termination, and a selection gene. An exemplary plasmid is YRp7, (Stinchcomb, et al. (1979) *Nature* 282:39; Kingsman, et al. (1979) *Gene* 7:141; Tschemper, et al. (1980) *Gene* 10:157). This plasmid contains the trpl gene, which provides a selection marker for a mutant strain of yeast lacking the ability to grow in tryptophan, for example ATCC No. 44076 or PEP4-1 (Jones (1977) *Genetics* 85:12). The presence of the trp1 lesion in the yeast host cell genome then provides an effective environment for detecting transformation by growth in the absence of tryptophan.

Cultures of cells derived from multicellular organisms are also desirable hosts for recombinant protein synthesis. In principal, any higher eukaryotic cell culture is workable, whether from vertebrate or invertebrate culture, including insect cells. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment that also contains the SV40 viral origin of replication. See Fiers, et al. (1978) *Nature* 273:113. Further, the protein promoter, control and/or signal sequences may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Host cells such as insect cells (e.g., cultured *Spodoptera frugiperda* cells) and expression vectors such as the baculovirus expression vector (e.g., vectors derived from *Autographa californica* MNPV, Trichoplusia ni MNPV, *Rachiplusia ou* MNPV, or *Galleria ou* MNPV) may be employed to make proteins useful in carrying out the present invention, as described in U.S. Pat. Nos. 4,745,051 and 4,879,236. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

In mammalian host cells, a number of viral-based expression systems may be utilized. In cases where an adenovirus is used as an expression vector, sequences encoding an rPAI-1 may be ligated into an adenovirus transcription/translation complex consisting of the late promoter and tripartite leader sequence. Insertion in a non-essential E1 or E3 region of the viral genome may be used to obtain a viable virus which is capable of expressing the rPAI-1 in infected host cells (Logan and Shenk (1984) *Proc. Natl. Acad. Sci.* 81:3655-3659). In addition, transcription enhancers, such as the Rous sarcoma virus (RSV) enhancer, may be used to increase expression in mammalian host cells.

Rather than using vectors that contain viral origins of replication, one may transform mammalian cells by the method of cotransformation with a selectable marker and the chimeric protein DNA. An example of a suitable selectable marker is dihydrofolate reductase (DHFR) or thymidine kinase. See U.S. Pat. No. 4,399,216. Such markers are proteins, generally enzymes, that enable the identification of transformant cells, i.e., cells which are competent to take up exogenous DNA. Generally, identification is by survival or transformants in culture medium that is toxic, or from which the cells cannot obtain critical nutrition without having taken up the marker protein.

Depending on the host cell to be transformed, any well-known means of introducing the expression vector containing nucleic acid sequences encoding an rPAI-1 may be used. Following the introduction of the expression vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, et al. (1977) *Cell* 11:223-32) and adenine phospho-ribosyltransferase (Lowy, et al. (1980) *Cell* 22:817-23) genes which can be employed in tk- or aprt- cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567-70); npt, which confers resistance to the aminoglycosides neomycin and G-418 (Colbere-Garapin, et al (1981) *J. Mol. Biol.* 150:1-14) and als or pat, which confer resistance to chlorsulfuron and phosphinotricin acetyltransferase, respectively. Additional selectable genes have been described, for example, trpB, which allows cells to utilize indole in place of tryptophan, or hisD, which allows cells to utilize histinol in place of histidine (Hartman and Mulligan (1988) *Proc. Natl. Acad. Sci.* 85:8047-51). Alternatively, visible such as anthocyanins, β glucuronidase and its substrate GUS, and luciferase and its substrate luciferin, may be used not only to identify transformants, but also to quantify the amount of transient or stable protein expression attributable to a specific vector system (Rhodes, et al. (1995) *Methods Mol. Biol.* 55:121-131).

Host cells transformed with nucleotide sequences encoding an rPAI-1 may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode an rPAI-1 may be designed to contain signal sequences which direct secretion of the rPAI-1 through a prokaryotic or eukaryotic cell membrane. Other constructions may be used to join sequences encoding an rPAI-1 to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp., Seattle, Wash.). The inclusion of cleavable linker sequences such as those specific for Factor XA or enterokinase (Invitrogen, San Diego, Calif.) between the purification domain and the rPAI-1 may be used to facilitate purification. One such expression vector provides for expression of a fusion protein containing an rPAI-1 and a nucleic acid encoding six histidine residues preceding a thioredoxin or an enterokinase cleavage site. The histidine residues facilitate purification on IMAC (immobilized metal ion affinity chromatography) (see, e.g., Porath, et al. (1992) *Prot. Exp. Purif.* 3:263-281) while the enterokinase cleavage site provides a means for purifying the rPAI-1 from the fusion protein. A discussion of vectors which contain fusion proteins is provided in Kroll, et al. (1993) *DNA Cell Biol.* 12:441-453).

In addition to recombinant production of the rPAI-1 isoforms may be produced by direct peptide synthesis using solid-phase techniques (Merrifield (1963) *J. Am. Chem. Soc.* 85:2149-2154). Protein synthesis may be performed using manual techniques or by automation. Automated synthesis may be achieved, for example, using Applied Biosystems 431A Peptide Synthesizer (Perkin Elmer). Various fragments of the rPAI-1 isoforms may be chemically-synthesized separately and combined using chemical methods to produce the full-length molecule.

Recombinant proteins provided herein may be used as isolated and substantially purified proteins in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the PAI-1 proteins may be incorporated into biodegradable polymers allowing for sustained release of the proteins, the polymers being implanted in the vicinity of where drug delivery is desired, for example, at the site of a tumor or implanted so that the rPAI-1 isoform is slowly released systemically. Osmotic minipumps may also be used to provide controlled delivery of high concentrations of rPAI-1 through cannulae to the site of interest, such as directly into a metastatic growth or into the vascular supply to that tumor. The biodegradable polymers and their use are described, for example, in detail in Brem et al. ((1991) *J. Neurosurg.* 74:441-446).

It is contemplated that the rPAI-1 isoforms of the present invention may be co-administered. For example, rPAI-$1_{23}$ and rPAI-$1_{A23}$ may be used in a combination therapy for enhancing the formation of angiostatin and/or modulating angiogenesis.

The rPAI-1 formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

It is further contemplated that the rPAI-1 isoforms may be administered via stem cells which are genetically engineered to produce the rPAI-1 isoform.

Cells to be targeted by the rPAI-1 protein formulations include, but are not limited to, an endothelial cell, a lymphocyte, a macrophage, a glia cell, a fibroblast, a liver cell, a kidney cell, a muscle cell, a cell of the bone or cartilage tissue, a synovial cell, a peritoneal cell, a skin cell, an epithelial cell, a leukemia cell or a tumor cell.

The present invention provides administration of an "effective amount" of rPAI-1 proteins to modulate angiogenesis or angiogenic processes or treat angiogenesis-mediated diseases. An "effective amount" is considered an amount of protein empirically determined to be necessary to achieve a reproducible change in cell proliferation or apoptosis (as determined by microscopic or macroscopic visualization and estimation of cell doubling time, or of nucleic acid synthesis assays) or migration (as determined by microscopic or macroscopic visualization) or in reducing the signs or symptoms of an angiogenesis-mediated disease as would be understood by one of ordinary skill in the art.

The specific amount of rPAI-1 protein required by each individual will be dependent upon the age, health, and weight of the recipient, kind of concurrent treatment, if any, frequency of treatment, and the nature of the effect desired.

The rPAI-1 isoforms of the present invention may be used to promote in vitro production of blood vessels for transplantation.

The rPAI-1 isoforms of the present invention are also useful in the formation of angiostatin containing K1-3 and/or K1-4. Angiostatin formation may be in vivo for therapeutic purposes or in vitro for recombinant, large-scale production of angiostatin with desired activity. It is contemplated that rPAI-1$_{23}$ and rPAI-1$_{A23}$ may be used alone or in combination to form the desired angiostatin.

The examples, which follow, are set forth to illustrate methods of the present invention, and are not to be construed as limiting thereof.

EXAMPLE 1

PAI-1 Gene Deletions

The DNA encoding the truncated PAI-1 proteins was obtained by deleting the porcine PAI-1 gene (poPAI-1) (Bijnens, et al. (1997) *Thromb. Haemost.* 77:350-356; Accession number Y11347; SEQ ID NO:11) . The selection of gene fragments was based on the poPAI-1 sequences that correspond to the human PAI-1 gene (huPAI-1) (Bosma, et al. (1988) *J. Biol. Chem.* 263:9129-9141; Accession number J03764; SEQ ID NO:12) sequence reported to code for functional domains in human PAI-1 (Reilly and Hutzelmann (1992) supra) . Each DNA fragment was isolated from porcine aortic endothelial cells by reverse transcribing RNA into cDNA. The cDNA was made double-stranded in a polymerase chain reaction (PCR) containing porcine PAI-1-specific primers. Primers for amplification of the cDNA encoding rPAI-1$_{23}$, were 5'-primer, 5'-GGAATTCAAGGAGCTATGG-3' (SEQ ID NO:13) and 3'-primer, 5'-GCTCTAGATTTCCACTGGTGATG-3' (SEQ ID NO:14). The resulting product corresponds to nucleotides 444-999 of poPAI-1 and 238-793 of huPAI-1. Primers used to PCR amplify the cDNA into double-stranded DNA coding for rPAI-1$_{A23}$ are 5' primer: 5'-G GAATTCATGGATGAGATCAGCACGG-3' (SEQ ID NO:15) and 3' primer: 5'-GC TCTAGATTTCCACTGGCTGATG-3' (SEQ ID NO:16) . The resulting product corresponds to nucleotides 471-999 of poPAI-1 and 265-793 of huPAI-1. Likewise, primers used to PCR amplify the cDNA into double-stranded DNA coding for rPAI-1$_{Hep23}$ are 5' primer: 5'-G GAATTCATGCAGTTCAAGATTGAGGAGAAGGGC-3' (SEQ ID NO:17) and 3' primer: 5'-GC TCTAGATTTCCACTGGCTGATG-3' (SEQ ID NO:18). The resulting product corresponds to nucleotides 390-999 of poPAI-1 and 184-793 of huPAI-1. Furthermore, primers used to PCR amplify the cDNA into double-stranded DNA coding for rPAI-1$_{24}$ are 5' primer: 5'-G GAATTCAAGGAGCTCATGG-3' (SEQ ID NO:19) and 3' primer: 5'-GC TCTAGATCAAGGCTCCATCAC-3' (SEQ ID NO:20). The resulting product corresponds to nucleotides 444-1346 of poPAI-1 and 238-1162 of huPAI-1. Underlined nucleotides denote restriction enzyme recognition sequences. PCR conditions for amplification of all three genes are known to one skilled in the art, for example, Reilly and Hutzelmann ((1992) supra). The PCR-amplified rPAI-1 DNA fragments were double-digested with EcoRI and Xba1 (Roche, Indianapolis, Ind.) to create overhangs. The restricted DNA was ligated into *Pichia pastoris* yeast shuttle vector pGAPZαA (INVITROGEN™, Carlsbad, Calif.). The TOP 10 strain of *Escherichia coli* was transformed by electroporation as described (Mulligan-Kehoe, et al. (2001) supra) . Following an overnight incubation at 37° C., colonies were selected and grown in low salt LB broth for 5-7 hours at 37° C. The DNA from each colony was isolated using a miniprep kit (Qiagen, Inc. Valencia, Calif.) to identify a clone containing each gene insert. Positive isolates were identified by restriction enzyme digests and were verified by sequencing. Each recombinant protein was expressed in *P. pastoris* as described (Reilly and Hutzelmann (1992) supra) and purified by affinity chromatography. The sequences of rPAI-1$_{23}$, rPAI-1$_{A23}$, rPAI-1$_{Hep23}$, and rPAI-1$_{24}$ DNA matched the known sequence of the corresponding segment of porcine PAI-1 DNA. Each rPAI-1 protein corresponded to its expected molecular weight.

EXAMPLE 2

Anti-Angiogenic Effects of rPAI-1 Proteins

Characterization of the rPAI-1 Protein Interactions with Heparin, uPA, and Plasminogen.

The functionality of the rPAI-1 proteins was first tested by incubating each truncated protein with uPA and plasminogen to assess the proteolytic activity of the products of the reaction, as known in the art, for example Mulligan-Kehoe, et al. ((2001) supra) . The functionality of each rPAI-1 isoform was then tested in a reaction with heparin bound to Sepharose beads. First, the rPAI-1$_{23}$, rPAI-1$_{A23}$, rPAI-1$_{Hep23}$, and rPAI-1$_{24}$ proteins (20 µg) were each incubated with 50 µl of heparin-bound Sepharose beads (Amersham Pharmacia Biotech, Piscataway, N.J.) for 2 hours at 37° C. The unbound protein was separated from the heparin-Sepharose-bound protein complex by microcentrifugation at 4° C. for 15 minutes. The proteins bound to the Sepharose beads were washed in TBS/Tween-20 followed by TBS washes. Bound samples were reacted with uPA (0.5 IU/1 µg or rPAI-1 protein) at 37° C. for 1 hour followed by a second one hour, 37° C. incubation with plasminogen (1 IU/1 µg of rPAI-1 protein) . The reaction samples were analyzed on a 15% SDS polyacrylamide gel containing 1.3% casein (zymogram) (Clowes, et al. (1990) *Circ. Res.* 67:61-67; Allaire, et al. (1998) *Circulation* 98:249-255). The electrophoresed samples were incubated overnight at 37° C. in 50 mM Tris-HCl, pH 7.9, buffer containing 5 mM CaCl$_2$ to enable plasmin degradation of casein.

Identification of Plasminogen Kringle Domains.

Protein products from the reaction of rPAI-1, uPA and plasminogen were electrophoresed on a 4-20% SDS polyacrylamide gel and transferred to nitrocellulose. The blots were probed with an antibody (1 µg/ml), specific for plasminogen kringles 1-3 (R&D Systems, Inc., Minneapolis, Minn.). Following a 1 hour, room temperature incubation with the primary antibody, a secondary rabbit anti-goat IgG HC+LC polyclonal antibody (Pierce, Rockford, Ill.) at a concentration of 1 µg/ml was incubated with the anti-kringle-probed membrane for 1 hour at room temperature. A horseradish peroxidase-conjugated antibody (donkey anti-rabbit IgG, Amersham, Arlington Heights, Ill.) diluted 1:5000 amplified the binding reaction which was ultimately detected by addition of a chemiluminescent substrate (Amersham Pharmacia).

In vitro Angiostatin Production in rPAI-1 Treated Cells. Bovine aortic endothelial cells (BAEC) were plated in six-well culture plates. When the cells reached confluence, fresh growth medium containing either rPAI-1$_{23}$ or rPAI-1$_{A23}$ (1.2 nM) was added; untreated endothelial cells served as the control. The cell culture media and the extracellular matrix with associated cells were collected from the untreated, rPAI-1$_{23}$-or rPAI-1$_{A23}$-treated BAEC in a 6, 15, 24, 36, 48, and 72 hour time course, using a standard method (Mulligan-Kehoe, et al. (2001) supra) . The concentration of protein in each sample from the time course was measured in a Bradford assay (Bradford (1976) *Anal. Biochem.* 72:248-254). Equivalent amounts of protein from each sample were analyzed for proteolytic activity on casein zymograms, using well-known methods (Mulligan-Kehoe, et al. (2001) supra).

Identification of plasminogen cleavage products from rPAI-1 protein, uPA, and plasminogen reactions. Either rPAI-$1_{23}$ or rPAI-$1_{A23}$ protein (3, 15, 30 nM) was incubated with two-chain uPA (0.5, 0.25, 0.05, 0.025 IU) for one hour at 37° C. Two-chain uPA is required for cleavage of plasminogen into plasmin. After one hour, plasminogen (1 IU) was added to the uPA/rPAI-1 reaction mix, and incubated for an additional one hour at 37° C. The order in which the reactants were added was varied, but in each case the incubation time and temperature remained the same. The permutations that were used were: 1) rPAI-1 protein and tcuPA, then plasminogen; 2) tcuPA and plasminogen, then rPAI-1 protein; 3) rPAI-1 protein, tcuPA, and plasminogen reacted simultaneously.

Reaction mixtures containing rPAI-1 protein, uPA and plasminogen were electrophoresed and transferred to nitrocellulose. The reaction mixtures were then used for immunoblot analysis. Immunoblots were probed with antibodies specific for different plasminogen epitopes. All primary antibodies were used at a concentration of 1 µg/ml. The plasminogen-specific antibodies were raised against either K1-3 (R&D Systems, Inc., Minneapolis, Minn.), K4 (American Diagnostica, Greenwich, Conn.), or mini-plasminogen (American Diagnostica). Mini-plasminogen is defined by the vendor as K5 plus the serine protease domain. The antibody to mini-plasminogen does not recognize complexed plasmin. The membranes were probed for K1-3. The membranes probed for K4 or mini-plasminogen were first incubated with 1 µg/ml of the epitope-specific primary antibodies for one hour at room temperature. Then a rabbit anti-mouse IgG HC+LC (Pierce, Rockford, Ill.) polyclonal antibody at a concentration of 1 µg/ml was incubated with each membrane for 1 hour at room temperature. A horseradish peroxidase-conjugated antibody (donkey anti-rabbit IgG, Amersham, Arlington Heights, Ill.) amplified the binding reaction which was ultimately detected by addition of a chemiluminescent substrate (Amersham Pharmacia).

Plasminogen cleavage products in reactions containing rPAI-1 and plasminogen. The rPAI-$1_{23}$ and rPAI-$1_{A23}$ proteins (3, 15, and 30 nM) were each incubated with plasminogen (1 Unit) for two hours at 37° C. The proteins were denatured at 100° C. for five minutes before electrophoresis on a 10-20% SDS, non-reducing, polyacrylamide gel. The proteins were transferred to a nitrocellulose membrane and probed for mini-plasminogen.

Binding interactions of rPAI-1 and uPA. Each rPAI-1 protein (3, 15, and 30 nM) was incubated with 0.5 IU of either scuPA or tcuPA for two hours at 37° C. The reaction mixture was electrophoresed on a 4-20%, SDS, non-reducing polyacrylamide gel. The proteins were transferred to nitrocellulose. The immunoblots were incubated for one hour at room temperature with 1 µg/ml of a monoclonal antibody raised against an epitope in the B-chain of uPA near the catalytic domain (American Diagnostica). This antibody recognizes single-chain and two-chain uPA. A secondary rabbit anti-mouse IgG HC+LC (Pierce, Rockford, Ill.) polyclonal antibody at a concentration of 1 µg/ml was incubated with the membrane for one hour at room temperature. A horseradish peroxidase-conjugated antibody (donkey anti-rabbit IgG, Amersham, Arlington Heights, Ill.) amplified the binding reaction which was ultimately detected by addition of a chemiluminescent substrate (Amersham Pharmacia).

Apoptosis Detection. Bovine aortic endothelial cells (BAEC) were plated at a density of $1.0 \times 10^6$ cells/T-75 culture flask containing Dulbecco's Modified Eagle's Medium (DMEM) (Gibco BRL, Gaithersburg, Md.) supplemented with 10% fetal bovine serum, penicillin/streptomycin (100 IU/ml), and L-glutamine (0.292 mg/ml) (Gibco BRL, Gaithersburg, Md.). The cells were incubated for 24 hours at 37° C., 5% $CO_2$ before adding 3 nM of either exogenous rPAI-$1_{23}$, rPAI-$1_{A23}$, rPAI-$1_{Hep23}$, rPAI-$1_{24}$ or supernatant from P. pastoris culture medium. The cells were incubated an additional 48 hour at 37° C. Adherent cells were trypsinized, resuspended in DMEM containing 10% FBS, and incubated at 37° C. for 10 minutes, then pelleted. The pelleted cells were washed twice with cold Hanks' balanced salt solution (HBSS). Fluorescein isothiocyanate (FITC) conjugated APOPNEXIN™ and propidium iodide (PI) were added to the cells following the manufacturer's protocol (Integren, Purchase, N.Y.) (Koopman, et al. (1994) Proc. Natl. Acad. Sci. USA 84:1415-1420). Each cell fraction was analyzed separately on a FACScan (Becton Dickenson, San Jose, Calif.). The data represent five separate experiments, each performed in duplicate.

Proliferation. Bovine endothelial cells, treated with exogenous rPAI-1 protein, were plated into 6-well culture plates at a density of $1.0 \times 10^4$/ml to assess their proliferative properties in the presence of rPAI-1 proteins. The cells were trypsinized and counted on a hemocytometer plate at 48 and 96 hours after adding exogenous rPAI-1. To further ascertain the proliferative properties of the rPAI-1-treated cells, a BrdU labeling assay was performed using a FITC-labeled BrdU-specific antibody. The addition of PI enabled a microscopic count of the proliferating cells relative to the total number of cells. BrdU was added to the culture medium to obtain a final concentration of 10 µM. Cells were incubated for 30 minutes at 37° C. in a $CO_2$ incubator and then washed twice in phosphate buffered saline (PBS) containing 1% bovine serum albumin (BSA). FITC-conjugated anti-BrdU was diluted 2.5-fold in 0.5% Tween 20/PBS and added directly to the cell culture medium for 30 minutes at room temperature. The cells were washed in PBS and incubated with PI for 1 minute. Incorporation of BrdU was calculated by counting the number of cells containing FITC stain (green) or PI stain (red) in 5 fields/sample in triplicate experiments.

RPAI-1 Effect on Tubule Formation in a Chick Aortic Arch Ring Assay.

Aortic arches were removed from fertilized chicken eggs (Oliver Merrill & Sons, Londonderry, N.H.) at day 14 of embryonic development. The eggs were cracked into a sterile 100 mm culture dish. The embryo was removed from its surroundings by cutting away the associated membranes and yolk sac. The chick embryo was placed ventral side up to surgically expose the heart and aortic arches. The heart and aortic arch were removed and placed into a sterile culture dish containing PBS to which 1% penicillin/streptomycin (Gibco BRL, Gaithersburg, Md.) was added. Arches, from which the surrounding adventitia had been removed, were cut into 0.8 mm sections. Each arch was placed into 1-5 µl of MATRIGEL™ (Kleinman, et al. (1982) Biochemistry 21:6188-6193) that was deposited on the bottom of a 6-well culture plate just prior to adding the ring. An additional 10 µl of ice-cold MATRIGEL™ was spread in a circle surrounding each aortic arch. The MATRIGEL™ was allowed to solidify before adding 2 ml of human endothelial-SFM basal growth medium (Gibco BRL). An rPAI-1 protein and bovine brain extract (BBE) (Clonetics, San Diego, Calif.), at 30 nM and 10%, respectively were added to each well and incubated at 37° C., 5% $CO_2$. In order to assess the characteristics of the new sprouts that could be ascribed to VEGF and the characteristics that were inhibited by rPAI-$1_{23}$, VEGF-A (100 ng/ml) and rPAI-$1_{23}$ (30 nM) were added to the culture medium containing the aortic rings. At 48 hour, additional medium containing BBE or VEGF and rPAI-1 protein was added to the aortic rings. Growth at 37° C. was continued for an additional 48 hours. Quantitative evaluation of tubule formation was performed by a blinded observer on a scale of 1-5 (least to maximum sprouting).

In experiments with rPAI-1$_{23}$ and rPAI-1$_{A23}$, when cells reached confluence, they were placed in separate wells and treated with; rPAI-1$_{23}$ or rPAI-1$_{A23}$ (0.6 nM), rPAI-1$_{23}$ or rPAI-1$_{A23}$ (0.6 nM) and 0.25 units of either scuPA or tcuPA; or a reaction containing rPAI-1$_{23}$ or rPAI-1$_{A23}$ (0.6 nM) incubated with 0.25 units of either scuPA or tcuPA for one hour at 37° C. Following 24 hours of treatment, the culture medium was removed, the cells were washed in HBSS, and isolated in 1 ml of cell dissociation buffer (Sigma, St. Louis, Mo.). The viable cells in each sample were counted and $1 \times 10^5$ cells from each sample were added to triplicate six-well plates coated with MATRIGEL™. The cells were incubated for an additional 24 hours at 37° C. Each well was photographed with a 35 mm camera at 40× and 200× magnification under a Nikon inverted microscope.

EXAMPLE 3

VEGF-A Interactions

Biochemical Interactions of a VEGF-Heparin Complex with rPAI Proteins, uPA, and Plasmin.

VEGF was isolated from bovine aortic endothelial cells by first incubating the cells overnight in serum-free DMEM. The medium was changed before adding 100 μg/ml heparin (Sigma, St. Louis, Mo.) for 4 hours at 37° C. The serum-free DMEM containing the VEGF-heparin complex was precipitated in 80% ethanol. The serum-free medium from which the VEGF-heparin complex was isolated, was probed for VEGF-A$_{121}$ (Santa Cruz Biotechnology, Inc., Santa Cruz, Calif.) to insure that his non-heparin-binding VEGF isoform did not precipitate with the VEGF-heparin complex. VEGF-A$_{121}$ was not detected. The heparin-VEGF complex was incubated with rPAI-1$_{23}$, rPAI-1$_{A23}$, rPAI-1$_{Hep23}$, or rPAI-1$_{24}$ protein (3, 15, and 30 nM) for 2 hours at 37° C. Either uPA (0.25 IU) or plasmin (made from 1.0 IU plasminogen and 0.25 IU uPA) was added to the VEGF-heparin-rPAI-1 reaction. After an additional 2 hours incubation at 37° C. with uPA or plasmin, DTT, at a final concentration of 0.1 M, was added to one half of the reaction mixture for 3.5 hours at 37° C. An equal volume of each reaction mixture was denatured at 95° C., then electrophoresed on a 4-20% SDS polyacrylamide gel. The VGEF in each sample was visualized on a nitrocellulose membrane probed with monoclonal antibody to human VEGF-A$_{165, 189, 206}$ (BD PharMingen, San Diego, Calif.). A secondary rabbit anti-mouse IgG HC+LC polyclonal antibody (Pierce, Rockford, Ill.) was diluted to 1 μg/ml in TBS, pH 8.0, containing 5% skim milk, and incubated with anti-VEGF probed membranes for 1 hour at room temperature. A horseradish peroxidase-conjugated antibody (donkey anti-rabbit IgG, Amersham, Arlington Heights, Ill.) diluted 1:500 amplified the binding reaction which was ultimately detected by addition of a chemiluminescent substrate (Amersham, Arlington Heights, Ill.).

VEGF-A in the Culture Medium of rPAI-1-Treated Endothelial Cells. Bovine aortic endothelial cells were seeded into six-well culture plates and grown to confluence in DMEM. The confluent (quiescent) cells were treated with a single dose of rPAI-1 protein at a final concentration of 1.2 nM. At 6, 12, 15, 24, 30, 48, and 72 hours after the onset of treatment, the culture medium was removed from cells treated with each rPAI-1 protein. Equivalent amounts of protein were incubated with 0.1 M DTT for 2.5 hours at 37° C. The protein samples were electrophoresed on a 4-20% gradient, SDS-polyacrylamide gel. The proteins were transferred to a nitrocellulose membrane and probed for VEGF-A$_{165, 189, 206}$.

VEGF-A Bound to Heparan Sulfate in rPAI-1-treated Endothelial Cells. Bovine aortic endothelial cells were seeded into six-well culture plates and treated with rPAI-1 proteins. Following a 6-and 12-hour incubation with the rPAI-1 proteins, the culture medium was removed, the cell layer was washed twice in HBSS. The cells were incubated for 1 hour at 37° C. in 1 ml of HBSS-containing 0.05 IU of heparinase III (Sigma, St. Louis, Mo.). Following the incubation, the HBSS-containing proteins released during the enzymatic digest were collected. The proteins were concentrated in 80% ethanol. An equivalent amount of protein from each sample was incubated with 0.1 M DTT at 37° C. for 2.5 hours prior to electrophoresis in a 4-20% gradient SDS-polyacrylamide gel. The separated proteins were transferred to an immunoblot and probed for VEGF-A using an antibody specific for epitopes common to VEGF-A$_{165, 189, 209}$ (BD Pharmingen, San Diego, Calif.). In another series of experiments the immunoblots were probed simultaneously with two competing antibodies to VEGF-A; one antibody was specific for the active site of VEGF-A$_{165}$ (R&D Systems, Inc., Minneapolis, Minn.) and the second antibody was raised against an epitope common to VEGF-A$_{165, 189, 206}$. The binding reactions occurred at 4° C. for 15 hours. The binding reaction was further amplified, as described herein. The chemiluminescent detection was performed, as described herein.

EXAMPLE 4

Apoptosis in rPAI-1$_{23}$-Treated BAEC vs PAEC

Bovine aortic endothelial cells (BAEC) and porcine aortic endothelial cells (PAEC) were selected for comparison of apoptosis based on the expression of VEGFR-1 and VEGFR-2. BAEC express both receptors and PAEC does not express either receptor (Gille, et al. (2001) *J. Biol. Chem.* 276:3222-3230). BAEC and PAEC were seeded into T-25 flasks containing DMEM supplemented with 10% fetal bovine serum, penicillin/streptomycin (100 IU/ml), and L-glutamine (0.292 mg/ml). The cells were incubated at 37° C., 5% $Co_2$ until the cells reached confluence, at which time fresh culture medium containing 2.4 mM rPAI-1$_{23}$ was added to the cells. The treated cells continued to grow for an additional 36 hours before harvesting for analysis of apoptosis in an Annexin V assay.

EXAMPLE 5

Growth Factor-Independent Activity of rPAI-1$_{Hep23}$.

Ex vivo Assay.

The aortic arch was surgically removed from 14-day-old chick embryos, and sectioned into rings of approximately 0.8 mm. The rings were placed on MATRIGEL™ to promote tubule formation in endothelial-SFM basal growth medium containing 10% fetal bovine serum and either bFGF/VEGF (each at 50 ng/ml) or rPAI-1$_{Hep23}$ (15 nM). Growth of tubules was at 37° C., 5% $CO_2$ for 4 days. At day 2, additional medium containing growth factors or rPAI-1$_{Hep23}$ was added.

In vivo Assay.

The rPAI-1$_{23}$ protein, at a concentration of 20 μg/ml, was added to 0.5 ml of MATRIGEL™ containing 25 ng/ml of VEGF and bFGF. The rPAI-1$_{Hep23}$ protein (20 μg/ml) was added to the MATRIGEL™ in the absence of bFGF/VEGF.

The mixtures were kept on ice. Each test sample was injected into the right flank of eight C3H female mice. Neoangiogenic vessels were allowed to form around and into the MATRI-GEL™ plug for two weeks. At the end of the test period, the MATRIGEL™ pellets were surgically removed from the animals and fixed in 2.5% paraformaldehyde. The fixed pellets were embedded in paraffin from which sections were cut. Neoangiogenic vessels were counted in five sections prepared from each pellet.

EXAMPLE 6

Plaque Regression and Treatment of Atherosclerosis

Animals.

Female B6; 129S-Apob$^{tm2Sgy}$ Ldlr$^{tm1Her}$/J mice (LDLR$^{-/-}$/ApoB-100)(Jackson Laboratories, Bar Harbor, Me.) were used for all experiments. This strain was selected because it is reported to more closely mimic human atherosclerosis than other models (Farese, et al. (1996) *Proc. Natl. Acad. Sci. USA* 93:6393-6398). This strain expresses only apoliporotein B-100 (ApoB-100) and is deficient in low density lipoprotein receptor (LDLR).

Recombinant rPAI-1$_{23}$ Protein Production and Purification.

Recombinant, truncated PAI-I protein, rPAI-I$_{23}$, was produced, purified and tested for bacterial, yeast and endotoxin contaminants as described herein.

Diet and Treatment. Fifteen mice were fed Paigen's atherogenic diet (Paigen, et al. (1985) Atherosclerosis 57:65-73 without cholate (20% protein, 45% carbohydrate, 35% fat, no cholate) and four were fed a normal chow diet for a total of 20 weeks. Daily intraperitoneal injections of rPAI-I$_{23}$ ($5.4 \times 10^{-3}$ mg/kg/day) were delivered to eight age-matched and weight-matched female mice beginning at week 14 of a high fat, high cholesterol diet while 7 received saline treatment. The animals were examined daily and weighed weekly. Animal care and procedures were performed in accordance with the guidelines of the Animal Care and Use Committee and procedures outlined in the *Guide for the Care and Use of Laboratory Animals* (NIH publication No. 86-23, 1985).

Preparation of Tissue.

At 42 days of rPAI-I$_{23}$ treatment the animals were fasted overnight, then given an injection of 0.1 ml of ketamine per 30 grams of weight. The chest was opened and blood was drawn by heart puncture. The mice were euthanized, perfused with PBS followed by 4% paraformaldehyde under 110-120 mm/Hg pressure. The aortic root, and descending aorta were surgically removed, stained with Sudan IV and destained in 80% ethanol. The descending aorta and aortic root were cut longitudinally and en face whole mounts were prepared. The whole mounts were scanned at 3× magnification on a scanner. The total area of the artery and the Sudan IV-stained area were measured with SCION imaging software (Scion Corporation, Frederick, Md.) (n=8 for rPAI-I$_{23}$, high fat, high cholesterol treatment group; n=7 for saline, high fat, high cholesterol group; n=4 for saline, chow diet control).

For left carotid artery cross-sectional measurements, the left carotid artery was removed at the interface with the aortic root and placed upright in optimal cutting temperature (O.C.T.) tissue embedding compound (Salcura Finetek USA, Inc., Torrance, Calif.). Eight-micron serial sections began after a 30-micron section at the base of the aortic arch. Sectioning continued through the plaque region. The bifurcation of the left carotid artery and innominate artery was the point of reference for consistent measurements among all mice. N=7 for rPAI-I$_{23}$, high fat, high cholesterol treatment group; n=4 for saline, high fat, high cholesterol group; n=4 for saline, chow diet control.

Plasma Cholesterol Measurement.

Blood samples were anti-coagulated and stabilized by collecting into 1M EDTA, pH 7.5. Blood samples were incubated for 20 minutes at room temperature, centrifuged at 1000×g (Beckman Coulter centrifuge, Fullerton, Calif.) at 4° C. and plasma was collected (supernatant). The plasma cholesterol levels were determined by enzymatic assay using commercially available reagents (Raichem, San Diego, Calif.).

Confocal Microscopy and Vessel Reconstruction.

The animals were perfused as described, the descending aorta was removed with a wide margin to enable detection of angiogenic vasa vasorum. Aortas were probed with a rat anti-mouse CD31 monoclonal antibody (1 μg/ml) (BD BIO-SCIENCE) in an overnight incubation at 4° C. A fluorescein-conjugated goat anti-rat polyclonal antibody (INVITRO-GEN) amplified the binding reaction in a 1-hour room temperature incubation. CD31-probed vessels were imaged on a ZEISS LSM-510 META point scanning confocal microscope and Z-stacks were collected (40× objective, 0.7 scan zoom, 135 μM pinhole, 325.8×325.8×9.0 μM stack size). The aortas were then stained with Sudan IV and cut longitudinally for en face whole mounts as described. Images of plaque lipid and CD31-positive vessels were collected in confocal microscopic Z-stacks. The vessel volume for all mice within a group was measured by reconstructing the confocal Z-stack images using VELOCITY V.3.7 software (Improvision, Coventry, UK).

Fractal Analysis of Vessel Size.

Projection images of the CD31-stained vasa vasorum from the Z-stack reconstruction preformed with the VELOCITY software were transformed to black and white images using the thresh holding tool in VELOCITY. Fractal analysis was applied to the black and white images using a MatLAB script that implements the box counting method. The MatLAB script developed for analyzing fractal dimension automatically subtracts background, adjusts brightness and contrast, and implements Otsu's method (Otsu (1979) Transactions on Systems, Man, and Cybernetics 9: 62-66) for automated thresholding of segment data into vessel and non-vessel. The script then counts the number of boxes containing vessel (N), starting at a box size (S) ranging from one pixel to 128 by 128 pixels. Fractal dimension is calculated by linear regression of the log(S) vs. log(NS), as one minus the slope. The MatLAB script calculates the fractal dimension of the unskeletonized image, then skeletonizes the image and recalculates the fractal dimension (Bein, et al. (2004) *Am. J. Physiol. Cell Physiol.* 287:C1012-1022; Helisch, et al. (2006) *Arterioscler. Thromb. Vasc. Biol.* 26:520-526; Yu, et al. (2005) *Proc. Natl. Acad. Sci. USA* 102:10999-11004). Total vessel area and vessel length were measured by MatLab script. The vessel area is the unskeletonized image and is the sum of white pixels in a field. Length is same measurement, but on the skeletonized image.

Histologic Measurements of Plaque Morphology.

The left carotid artery was stained with hematoxylin and eosin. Vessel circumference, plaque area and lumen area were measured using SCION Image software.

Example 7

Pancreatic Tumor Vessel and Tumor Growth Inhibition

T3M4 pancreatic tumor cells, at a concentration of $1.5 \times 10^6$, were injected subcutaneous in the left rear dorsum of six age- and weight-matched female Balb/c nu/nu athymic mice (Charles River Laboratories). Animal care and procedures were performed in accordance with the guidelines of the Animal Care and Use Committee and procedures outlined in the Guide for the Care and Use of Laboratory Animals (supra). The mice were observed daily for tumor growth. At the end of 4 days, four of the six mice had a visible tumor with a geometric mean diameter (GMD) of 3.7±0.6 mm and a mean area of 13.8±2.6 mm$^2$. The mice were separated into two groups with equal distribution of tumor size into each group. One group received a daily intraperitoneal (IP) injection of rPAI-1$_{23}$ protein at a dose of $5.4 \times 10^{-3}$ mg/kg/day, while the remaining three received daily IP injections of 100 μl of saline. Data were calculated as mean±standard error of the mean (SEM) and p values were determined by student t-test.

The rPAI-1$_{23}$ protein was produced, purified and evaluated for yeast, bacterial and endotoxin contamination, as described herein.

The T3M4-derived tumor model was selected, because it is a fast growing tumor and would significantly challenge the anti-angiogenic effects of rPAI-1$_{23}$. After 5 days of treatment all animals were anesthetized with Ketamine (80 mg/kg)/Xylazine (10 mg/kg) and at the same time were heparinized, to ensure effective removal of their blood volume during perfusion. A 21 G butterfly needle was inserted into the descending aorta and the inferior vena cava was cut to allow for venus drainage. The animals were perfused with phosphate-buffered saline (PBS) until all of the visceral blood volume was flushed out and the perfusate drained through the arterial vent was essentially free of blood. Adequate perfusion was characterized by severe blanching of all visceral organs. When the PBS perfusion was complete, the silicone rubber (e.g., Microfil MV-122 Yellow) was infused through the aortic cannula by a syringe. Microfil compound infusion was continued until the injection mass flowed freely from the atrial vent and all organs had a rich yellow coloration and the animals were placed under refrigeration to allow polymerization. The tumors were then scanned using a GE EXPLORE LOCUS SP micro-CT scanner. After optimizing the scanning protocol for soft tissue imaging, the animals were scanned at a voltage and current of the X-ray tube of 55 kV and 120 mA, respectively. The X-ray exposure time for a single projection was set to 1700 ms and a total of 720 projections per scan were acquired at the maximum resolution of the X-ray detector, 6.5 microns. Following the scan, three-dimensional volumetric images were reconstructed from the acquired two dimensional projections by averaging every two neighboring pixels, yielding a voxel size of 13 microns.

What is claimed is:

1. A method for decreasing angiogenesis comprising administering an effective amount of a plasminogen activator inhibitor type 1 isoform lacking a reactive center loop and lacking a heparin-binding domain so that angiogenesis is decreased, wherein the amino acid sequence of said plasminogen activator inhibitor type 1 isoform is set forth in SEQ ID NO:3 or SEQ ID NO:7.

2. A method for decreasing angiogenesis comprising administering an effective amount of a plasminogen activator inhibitor type 1 isoform lacking a reactive center loop and lacking at least a portion of a heparin-binding domain so that angiogenesis is decreased, wherein the plasminogen activator inhibitor type isoform inhibits the release of VEGF from a VEGF-heparin complex thereby decreasing angiogenesis and wherein the amino acid sequence of said plasminogen activator inhibitor type 1 isoform is set forth in SEQ ID NO:4 or SEQ ID NO:8.

3. A method of promoting plaque regression comprising administering an effective amount of a plasminogen activator inhibitor type isoform lacking a reactive center loop and lacking at least a portion of the heparin-binding domain thereby promoting plaque regression, wherein the amino acid sequence of said plasminogen activator inhibitor type 1 isoform is set forth in SEQ ID NO:4 or SEQ ID NO:8.

4. A method of inducing angiostatin formation comprising administering an effective amount of a plasminogen activator inhibitor type isoform lacking a reactive center loop and lacking a heparin-binding domain so that the formation of angiostatin is induced, wherein the amino acid sequence of said plasminogen activator inhibitor type 1 isoform is set forth in SEQ ID NO:3 or SEQ ID NO:7.

5. A method of treating an angiogenesis-mediated disease comprising administering an effective amount of a plasminogen activator inhibitor type isoform lacking a reactive center loop and lacking at least a portion of a heparin-binding domain so that the signs or symptoms associated with the angiogenesis-mediated disease are reduced, wherein the amino acid sequence of said plasminogen activator inhibitor type 1 isoform is set forth in SEQ ID NO:4 or SEQ ID NO:8.

* * * * *